United States Patent [19]

Sutton

[11] Patent Number: 5,262,297
[45] Date of Patent: Nov. 16, 1993

[54] SPECIFIC BINDING ANALYTICAL AND SEPARATION METHODS USING CARBOXY CONTAINING POLYMERS

[75] Inventors: Richard C. Sutton; Susan J. Danielson; John B. Findlay; Fred T. Oakes; Marsha D. B. Oenick, all of Rochester; Ignazio S. Ponticello, Pittsford; Harold C. Warren, III, Rush, all of N.Y.

[73] Assignee: Eastman Kodak Company, Rochester, N.Y.

[21] Appl. No.: 876,672

[22] Filed: Apr. 30, 1992

Related U.S. Application Data

[62] Division of Ser. No. 539,774, Jun. 18, 1990, Pat. No. 5,147,777.

[51] Int. Cl.$^5$ ............... G01N 83/545; G01N 33/546; G01N 33/547
[52] U.S. Cl. .................... 435/5; 436/531; 436/532; 436/533; 436/534; 436/536; 436/538; 436/541; 436/804; 436/814; 436/817; 436/818; 436/824; 435/6; 435/7.22; 435/7.32; 435/7.34; 435/7.9; 435/7.92; 435/7.93; 435/7.94; 526/317.1; 526/318.4; 526/301; 526/314; 530/412; 530/413
[58] Field of Search ............... 436/531–534, 436/536, 538, 541, 804, 810, 814, 817, 818, 824; 435/5, 7.22, 7.32, 7.34, 7.9, 7.92, 7.93, 7.94, 6; 428/403, 407; 526/317.1, 318.4, 301, 314, 286; 530/412, 413

[56] References Cited

U.S. PATENT DOCUMENTS

| | | | |
|---|---|---|---|
| 3,616,229 | 10/1971 | Wildi et al. | 195/63 |
| 3,857,931 | 12/1974 | Hager | 424/12 |
| 4,039,652 | 8/1977 | Adams et al. | 436/541 |
| 4,101,549 | 7/1978 | Focella et al. | 424/12 |
| 4,138,383 | 2/1979 | Rembaum et al. | 526/227 |
| 4,140,662 | 2/1979 | Recket et al. | 424/12 |
| 4,181,636 | 1/1980 | Fischer | 435/181 |
| 4,235,867 | 11/1980 | Thoma | 424/12 |
| 4,264,766 | 4/1981 | Fischer | 536/51 |
| 4,352,884 | 10/1982 | Nakashima et al. | 435/180 |
| 4,766,062 | 8/1988 | Diamond et al. | 436/501 |
| 4,874,691 | 10/1989 | Chandler | 422/58 |
| 4,952,520 | 8/1990 | Okusa et al. | 436/824 |
| 4,962,154 | 10/1990 | Pollock et al. | 436/534 |
| 4,997,772 | 3/1991 | Sutton et al. | 436/533 |

Primary Examiner—Esther L. Kepplinger
Assistant Examiner—Christopher L. Chin
Attorney, Agent, or Firm—J. Lanny Tucker

[57] ABSTRACT

Specific binding methods are used for diagnostic assays and purification separations whereby the specific binding capture reagent is prepared from copolymers having highly reactive carboxy groups. These groups are extended from the polymer surface with a linking group having from 8 to 50 atoms in the chain and two or more alkylene, arylene, alkylenearylene or arylenealkylene groups. To these reactive groups is attached a biologically active substance such as a protein or oligonucleotide which then participates in the diagnostic assays or purification separation methods.

17 Claims, No Drawings

SPECIFIC BINDING ANALYTICAL AND SEPARATION METHODS USING CARBOXY CONTAINING POLYMERS

RELATED APPLICATION

This is a divisional of U.S. Ser. No. 07/539,774 filed Jun. 18, 1990, now U.S. Pat. No. 5,147,777.

Reference is made to copending and commonly assigned U.S. Ser. No. 539,768, filed on Jun. 18, 1990, now abandoned by Ponticello and Sutton and entitled "Carboxy Containing Monomers and Polymers and Latices Prepared from Same".

FIELD OF THE INVENTION

The present invention relates to biologically active reagents prepared using polymeric particles. It also relates to analytical elements containing such reagents, and to immunoassays and specific binding analytical methods using them. Further, it relates to an analytical purification method using the reagents. This invention can be used for various clinical, diagnostic, medical and research purposes.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable and suitable for automation or for use with test kits which can be readily used in doctors' offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses), but other specific binding reactions (such as between avidin and biotin and a sugar with a lectin) are well known.

Methods in the art using specific binding reactions generally require that one or more or both of the reactants be immobilized on a solid substrate of some type, so that unreacted (and generally water soluble) materials can then be separated from the water insoluble reaction product (often called a "complex"). In addition, such immobilized reactants can be used in affinity chromatography to remove a desired biologically active material from a mixture of such materials.

Biologically active substances have thus been immobilized to advantage on particulate substrates such as polymeric particles, animal and human erythrocytes, bacterial cells and other solid materials known in the art. For example, carrier particles prepared from epoxy group containing monomers are described in U.S. Pat. No. 4,415,700 (issued Nov. 15, 1983 to Batz et al).

Where polymeric particles have been used as carrier substrates, biologically active substances have been attached through reactive groups on the particle surface, such groups provided either from the polymer composition or from linking moieties attached to the particles. U.S. Pat. No. 4,401,765 (issued Aug. 30, 1983 to Craig et al) describes a number of reactive groups on polymeric particles.

Several advances in the art in this regard are described in U.S. Ser. No. 081,206 (filed Aug. 3, 1987 by Sutton et al now abandoned), U.S. Ser. No. 136,165 (filed Dec. 18, 1987 by Burdick et al now abandoned) and EP-A-0 308 235 (published Apr. 26, 1989 and corresponding to U.S. Ser. No. 373,304, filed Jun. 29, 1989 by Sutton et al as a CIP of U.S. Ser. No. 098,429, filed Sep. 18, 1987 now abandoned). These applications describe various means for attaching biologically active substances to polymeric particles having various reactive surface groups, including surface carboxy groups, such as groups provided by acrylic and methacrylic acids.

Carboxylated latex particles have also been used to prepare diagnostic reagents, as noted in U.S. Pat. No. 4,181,636 (issued Jan. 1, 1980 to Fischer) The described particles are prepared using a carboxyl-containing monomer such as acrylic acid, methacrylic acid, itaconic acid, aconitic acid, fumaric acid or maleic acid. Similar particles are described in U.S. Pat. No. 3,857,931 (issued Dec. 31, 1974 to Hager), U.S. Pat. No. 4,138,383 (issued Feb. 6, 1979 to Rembaum et al) and U.S. Pat. No. 4,264,766 (issued Apr. 28, 1981 to Fischer).

Two commercially available monomers, 3-acrylamido-3-methylbutanoic acid and 2-acrylamido-2-hydroxyacetic acid, have been polymerized to form polymers. These monomers are generally water-soluble and are difficult to copolymerize with oleophilic monomers and are not readily polymerized to form monodisperse particles.

Another advance in the art relates to the use of specific compounds to attach biological materials to particulate substrates having reactive carboxy groups. Generally, water-soluble carbodiimides have been used, as described in the references noted above. More recently, however, carbamoylonium compounds have been used for this purpose with considerable advantages, as described in U.S. Ser. No. 373,304 (filed Jun. 29, 1989 by Sutton et al) as a CIP of U.S. Ser. No. 286,097 (filed Dec. 19, 1988 now abandoned) which is a CIP of U.S. Ser. No. 098,429 (filed Sep. 18, 1987 now abandoned). Dication ethers are also known to be useful, as described in U.S. Ser. No. 389,390, (filed Aug. 3, 1989 by Scensny and Chen).

The modification of protein adsorption on polymeric surfaces has been a common goal for many workers trying to apply polymer technology to in vivo and in vitro uses in biotechnology. Undesirable protein adsorption has been a continual problem. For example, nonspecific adsorption is a major concern in the use of polymers for affinity chromatography for the purification of proteins.

The modification of polymer surfaces has taken many forms, including physical coatings, graft copolymerization, chemical treatments and plasma gas discharge treatment. The hydrophilic nature of the polymer surface has been the subject of considerable debate and research because an increase in hydrophilicity reduces adsorption of some proteins, but not others. As noted in the art cited above, the use of reactive side chains has also received considerable attention in the art.

There is a need in the art to find new biological reagents which show improvement over the standard reagents prepared from standard carboxy-containing polymers. Such reagents would be especially useful having attached biological materials for use in research and various analytical and diagnostic procedures.

SUMMARY OF THE INVENTION

The problems noted with known reagents are overcome with a biologically active reagent comprising:

(I) a water-insoluble particle composed of, at least on its surface, a copolymer having recurring units derived from:
  (a) from about 60 to about 99.8 mole percent of one or more ethylenically unsaturated polymerizable oleophilic monomers which provide hydrophobicity to the copolymer,
  (b) from about 0.2 to about 40 mole percent of one or more ethylenically unsaturated polymerizable monomers having a reactive carboxy group, or salt thereof, and represented by the structure:

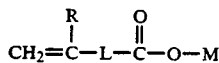

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, and
  (c) from 0 to about 15 mole percent of one or more additional ethylenically unsaturated polymerizable monomers other than those identified in categories (a) and (b) above, and
(II) a biologically active substance covalently attached to the particle through the reactive carboxy group or salt thereof.

This invention also provides an analytical element comprising a substrate having one or more reaction zones therein, and containing in at least one of the zones, a biologically active reagent as described above.

Moreover, a method for the determination of a specific binding ligand comprises:
A. forming a water-insoluble specific binding complex of a specific binding ligand of interest, or a receptor therefor, with a reagent comprising:
  (I) a water-insoluble particle composed of, at least on its surface, a copolymer having recurring units derived from:
    (a) from about 60 to about 99.8 mole percent of one or more ethylenically unsaturated polymerizable oleophilic monomers which provide hydrophobicity to the copolymer,
    (b) from about 0.2 to about 40 mole percent of one or more ethylenically unsaturated polymerizable monomers having a reactive carboxy group, or salt thereof, and represented by the structure:

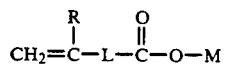

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, and
    (c) from 0 to about 15 mole percent of one or more additional ethylenically unsaturated polymerizable monomers other than those identified in categories (a) and (b) above, and
  (II) a biologically active substance covalently attached to the particle through the reactive carboxy group or salt thereof, said substance being specifically reactive with either the ligand or a receptor therefor, and
B. detecting the presence of the complex as an indication of the presence or amount of the ligand in the specimen.

This invention also provides an assay for the determination of a specific binding ligand comprising:
  detecting the presence or amount of a water-insoluble specific binding complex formed between a ligand of interest and a receptor therefor, the receptor provided as a component of a reagent comprising:
  (I) a water-insoluble particle composed of, at least on its surface, a copolymer as described above, and
  (II) the receptor for the ligand being covalently attached to the particle through the reactive carboxy group or salt thereof.

Still further, an immunoassay employing antibodies or antigens for detecting the presence or amount of a ligand in a specimen comprises addition of an immunoreactant which is specifically reactive with the ligand or with a receptor therefor,
  the immunoreactant being a component of a reagent comprising:
  (I) a water-insoluble particle composed of, at least on its surface, a copolymer as described above, and
  (II) the immunoreactant being covalently attached to the particle through the reactive carboxy group or salt thereof.

An analytical separation method of this invention comprises:
A. passing a specimen containing a mixture of biologically active substances over an affinity chromatography reagent comprising:
  (I) a water-insoluble particle composed of, at least on its surface, a copolymer as described above, and
  (II) a specific binding substance covalently attached to the particle through the reactive carboxy group, the specific binding substance being specific to one or more predetermined biologically active substances in the specimen mixture of biologically active substances to form a complex of the reagent with the predetermined substances, and
B. collecting either the one or more complexed predetermined substances or one or more substances remaining in the eluent.

The present invention provides reagents which are useful in a variety of analytical, diagnostic and purification methods. These reagents are improvements over known reagents prepared using standard carboxy containing polymers.

The advantages of the present invention are provided by the use of certain copolymers having a carboxy group which is extended from the copolymer surface by a sufficient length to allow improved results in the attachment of biologically active substances and their subsequent use. Thus, in the structure noted above, the organic group identified as "L" is critically from 8 to 50 carbon, nitrogen, oxygen and sulfur atoms in length.

The extended hydrophilic carboxy group on the monomers used to make the copolymers provide certain advantages over monomers having shorter carboxy groups which are known in the art. During emulsion polymerization, the improved monomers have less tendency to polymerize in the aqueous phase as solution (or water-soluble) polymers. Thus, the improved monomers are more easily and more completely incorporated into water-insoluble latex particles, and thereby facilitate attachment of proteins or other biological compounds. Latices prepared from acrylic acid contain unwanted soluble polymer in the aqueous phase, which for some uses, must be removed at considerable expense. The improved monomers described herein produce less water-soluble polymer.

Further, the reactivity ratios of the preferred monomers used in the practice of this invention, that is those having aromatic groups as part of L (such as styrene derivatives), are more favorable than known carboxy-containing monomers for polymerization with aromatic comonomers, such as styrene and styrene derivatives. Moreover, the extended linking group enables the carboxy groups to be more easily activated by carbodiimides or other activation agents when biological compounds are attached to the particles.

DETAILED DESCRIPTION OF THE INVENTION

The copolymers useful in the preparation of the reagents of this invention and methods of preparing same are described in detail in U.S. Ser. No. 539,768 of Ponticello and Sutton (noted above), abandoned in favor of CIP U.S. Ser. No. 654,112 filed Jun. 18, 1990), now U.S. Pat. No. 5,149,737. The following discussion is provided as a summary of these copolymers.

The copolymers of this invention have as an essential component recurring units derived from one or more ethlenically unsaturated polymerizable monomers having the following structure:

wherein R is hydrogen, halo or alkyl of 1 to 3 carbon atoms, M is hydrogen, an alkali metal ion or an ammonium ion and L is an organic linking group having from 8 to 50 carbon, oxygen, nitrogen or sulfur atoms in the linking chain. A mixture of monomers can be used if desired, although preferably only one such monomer is used to prepare each copolymer.

More specifically, in the structure noted above, R is hydrogen, halo (such as chloro or bromo) or alkyl of 1 to 3 carbon atoms (such as methyl, ethyl, isopropyl and n-propyl). More preferably, R is hydrogen or methyl.

Also, M is hydrogen, an alkali metal ion (such as lithium, sodium and potassium) or an ammonium ion (such as ammonium, tetramethylammonium and tetraethylammonium). Preferably, M is hydrogen or an alkali metal ion, and more preferably, it is hydrogen or sodium.

L is an organic linking group which has from 8 to 50 of a combination of carbon, nitrogen, oxygen or sulfur atoms in the chain. The linkage comprises two or more divalent hydrocarbon groups such as alkylene, arylene, alkylenearylene, arylenealkylene and similar groups which are connected or terminated with the noted heteroatoms or with heteroatom-containing groups such as carbonyl, sulfonyl, imino and others known in the art. Such hydrocarbon groups can have from 1 (such as methylene) up to 12 carbon atoms, and can be branched, linear or cyclical, substituted or unsubstituted with one or more alkyl groups (preferably of from 1 to 12 carbon atoms, such as methyl, ethyl, isopropyl, hexyl and octyl), alkoxy (preferably from 1 to 12 carbon atoms, such as methoxy, ethoxy, propoxy, t-butoxy and octyloxy), cycloalkyl (preferably from 4 to 6 carbon atoms, such as cyclobutyl, cyclohexyl and cyclopentyl), aryl (preferably from 6 to 12 carbon atoms, such as phenyl, tolyl, xylyl, naphthyl, 4-methoxyphenyl and chlorophenyl). Such groups are not difficult to design or synthesize for one skilled in synthetic chemistry.

Preferably, L comprises two or more alkylene or arylenealkylene groups which are connected or terminated with an oxy, thio, imino (—NR$^1$—), carbonyloxy (—COO—), carbonylimino (—CONR$^1$—), ureylene (—NR$^1$CONR$^1$—) or sulfonylimino (—SO$_2$NR$^1$—) group, wherein each R$^1$ in the noted groups is independently hydrogen, alkyl having 1 to 10 carbon atoms (such as methyl, ethyl, isopropyl, n-butyl, hexyl, benzyl and 2,4-dimethylpentyl), cycloalkyl having 4 to 10 carbon atoms in the backbone (such as cyclopentyl, cyclohexyl and 1,3-dimethylcyclohexyl) or aryl having 6 to 14 carbon atoms in the backbone (such as phenyl, xylyl, p-chlorophenyl, naphthyl and anthryl).

Representative L groups include, but are not limited to: p-phenylenemethyleneoxycarbonyltrimethylene, carbonyloxyethyleneoxycarbonyltrimethylene, carbonyloxyethyleneureylenepentamethylene, carbonylpenta(oxyethylene)oxycarbonyltrimethylene, carbonyldeca(oxyethylene)oxycarbonyltrimethylene, p-phenylenemethylenethioethyleneoxycarbonyltrimethylene, carbonyloxyethyleneiminocarbonyltrimethylene, carbonyloxytetramethyleneoxycarbonyltetramethylene, p-phenylenemethyleneiminocarbonyltrimethylene, p-phenylenemethyleneiminocarbonyltrimethylene, p-phenylene(methyl)iminoethyleneoxycarbonyltrimethylene, p-phenylenemethylenethioethylene, p-phenylenemethylenethioethyleneiminocarbonylmethyleneoxymethylene, p-phenylenemethylenethioethyleneiminocarbonylmethylenethiomethylene, p-phenylenemethylenethioethyleneiminocarbonyltrimethylene, phenylenemethylenethio-1-carboxyethylene, phenylenemethylenethiophenylene, phenylenemethylenethioethyleneoxyethylenethiomethyleneoxycarbonylethylene, phenylenemethyleneoxyphenylenemethylenethioethylene, phenylenemethylenethioethyleneoxyethylenethioethyleneoxycarbonylethylene, phenylenemethyleneoxyphenylenemethylenethiophenylenemethylenethiotrimethylene and phenylenemethylenethioethyleneoxyethylenethioethyleneoxycarbonylphenylene.

Representative monomers described by the structure identified above include, but are not limited to: mono-m & p-vinylbenzyl glutarate, mono-p-vinylbenzyl glutarate, mono-2-methacryloyloxyethyl glutarate, 2-(4-carboxybutyramido)ethyl methacrylate, 2-[N'-(5-carboxypentyl)ureido]ethyl methacrylate, mono-methacryloylpenta(oxyethylene) glutarate, mono-(4-acryloyloxybutyl) glutarate, 4-(4-carboxybutyramido)styrene, mono-methacryloyldeca(oxyethylene) glutarate, mono-2-(p-vinylbenzylthio)ethyl glutarate, mono-2-(m- & p-vinylbenzylthio)ethyl glutarate, 4-(4-carboxybutyramidomethyl)styrene, mono-2-[N-methyl-N-(4- vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-methacryloylpenta(oxyethylene) phthalate, mono-methacryloyldeca(oxyethylene) phthalate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio]benzylthio}butyric acid.

The most preferred monomer is 3-(p-vinylbenzylthio)propionic acid.

The monomers described above are generally copolymerized with one or more additional ethylenically unsaturated polymerizable monomers.

The oleophilic monomers identified above as (a) monomers are useful for providing hydrophobicity or water-insoluble properties to the resulting copolymer. A mixture of such monomers can be used if desired. Such monomers include, but are not limited to, vinyl aromatics (for example, styrene and styrene derivatives such as 4-vinyltoluene, α-methylstyrene, 2,5-dimethylstyrene, 4t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate vinyl bromide, vinylidene chloride and crosslinkable monomers having two or more polymerizable groups. Useful crosslinkable monomers include, but are not limited to, divinylbenzene, allyl acrylate and di- and triacrylates and methacrylates (such as 2,2-dimethyl-1,3-propylene diacrylate, 1,4-cyclohexylenedimethylene dimethacrylate, ethylene diacrylate, ethylene dimethacrylate, propylene diacrylate, propylene dimethacrylate, ethylidyne trimethacrylate) and others readily apparent to one skilled in polymer chemistry.

In addition, ethylenically unsaturated polymerizable monomers (c) other than those described above for monomers (a) or (b) can be copolymerized to provide desirable properties. For example, such monomers include anionic monomers containing sulfonic acid groups or salts thereof, including 2-acrylamido-2-methylpropane sulfonic acid, 3-methacryloyloxypropane-1-sulfonic acid, p-styrene sulfonic acid and salts thereof, and others readily apparent to one skilled in the art. Also included in the (c) group of monomers are nonionic hydrophilic monomers such as acrylamide, methacrylamide, N-isopropylacrylamide, 2-hydroxyethyl acrylate, 2-hydroxyethyl methacrylate, N-vinyl-2-pyrrolidone and others readily apparent to one skilled in the art. In addition, monomers having active methylene groups, such as 2-acetoacetoxyethyl methacrylate, and cationic monomers, such as N,N,N-trimethyl-N-vinylbenzylammonium chloride and 3-hydroxyethyl-1-vinylimidazolium chloride could be used, as well as many others too numerous to mention here. A skilled polymer chemist would be able to readily fashion useful polymers from hundreds of available or producible monomers using the teaching presented herein.

Generally, the copolymers of this invention are composed of recurring units derived from about 60 to about 99.8 mole % of (a), from about 0.2 to about 40 mole % of (b), and from 0 to about 15 mole % of (c). Preferred copolymers are prepared from about 85 to about 99.5 mole % of (a), from about 0.5 to about 15 mole % of (b), and from 0 to about 10 mole % of (c).

The copolymers of this invention are prepared using standard emulsion or suspension polymerization techniques, as described for example by Sorenson et al in *Preparative Methods of Polymer Science*, 2nd Ed. (1968), Wiley and Sons, New York, and Stevens, *Polymer Chemistry, An Introduction*, Addison Wesley Publishing Co., London, 1975, and certain preferred conditions are discussed in copending U.S. Ser. No. 539,768 of Ponticello and Sutton (noted above), abandoned in favor of CIP U.S. Ser. No. 654,112 (filed Jun. 18, 1990), now U.S. Pat. No. 5,149,737.

The copolymers described herein are used in particulate form in order to prepare the reagents of this invention. The average particle size can vary greatly depending upon reagent use. Generally, it is from about 0.01 to about 20 μm, and preferably from about 0.1 to about 10 μm.

The reagents of this invention have one or more biologically active substances covalently attached to the polymeric particles through the reactive carboxy groups on the outer surface of the particles. As used herein, the term "biologically active substance" is meant to include any organic compound which is found in a living organism or which is useful in the diagnosis, treatment or genetic engineering of cellular material or living organisms, and which has a capacity for interaction with another biological or chemical material. Such substances may or may not be naturally occurring in biological fluids. Such materials must be capable of attachment to the particles through the reactive carboxy groups using an appropriate activation agent, as described below. Thus, generally, this means that the biologically active substance has an available amino or sulfhydryl group for reaction.

Depending upon the intended use of the reagent, the biologically active substances can be from a wide variety of naturally occurring or synthetically prepared materials, including, but not limited to amines, enzymes, amino acids, peptides, polypeptides, proteins (including antibodies, C-reactive protein and avidin and its derivatives), lipoproteins, glycoproteins, hormones, drugs (for example digoxin, phenytoin, phenobarbital, thyroxine, triiodothyronine, gentamicin, carbamazepine and theophylline), steroids, vitamins, polysaccharides, glycolipids, alkaloids, microorganisms, viruses, protozoa, fungi, parasites, rickettsia, molds, blood components, tissue and organ components, pharmaceuticals, haptens, lectins, toxins, nucleic acids (including oligonucleotides, either single- and double-stranded), antigenic materials (including proteins and carbohydrates), biotin or derivatives thereof, and components of any of the materials just listed, and others known to one skilled in the art.

Particularly useful reagents of this invention are those in which the biologically active substance is a receptor molecule specific to a ligand of interest. Thus, a specific binding reaction involving the reagent can be used for various methods (described in more detail below). Examples of ligand receptor complexes (that is, reaction of the ligand and receptor) include, but are not limited to antibody-antigen, antibody-hapten, avidin-biotin, sugar lectin, gelatin-fibronectin and Protein A-IgG complexes. For purposes of this invention, complementary nucleic acids (that is, a hybridized product of complementary strands) are also considered specific binding materials. Such complementary nucleic acids (including oligonucleotides having at least 2 bases) need not be complementary at every base pair, nor must there be a matching base at every position in the nucleic acid sequence That is, one of the strands can be longer than the other, or one strand can have a plurality of oligonucleotides complementary thereto at difference sequences.

Most useful biologically active substances are what are known in the art as immunoreactive species which include: (1) any substance which, when presented to an immunocompetent host, will result in the production of a specific antibody capable of binding with that substance, or (2) the antibody so produced, which compound participates in an immunological reaction. Thus, the immunological species can be an antigenic material or an antibody (including anti-antibodies). Both monoclonal and polyclonal antibodies are useful, and they can be whole molecules or various fragments thereof, as long as they have at least one reactive site for reaction with the reactive carboxy groups on the particles.

Particularly useful biologically active substances include antibodies directed to Streptococcus A, a microorganism associated with periodontal disease, carbamazepine, thyroxine, human chorionic gonadotropin, phenobarbital, phenytoin, digoxin or a C-reactive protein.

In certain embodiments, the immunological species is an enzyme which has a reactive group for attachment. Representative enzymes include, but are not limited to, horseradish peroxidase, glucose oxidase, urease, $\beta$-galactosidase, aspartate aminotransaminase, alanine aminotransaminase, lactate dehydrogenase, creatine Phosphokinase, $\gamma$-glutamyl transferase, alkaline phosphatase, acid phosphatase and prostatic acid phosphatase.

In other embodiments, such as for competitive binding assays for determination of drugs or pregnancy, the biologically active substance is an antibody directed to human chorionic gonadotropin, phenobarbital, phenytoin or digoxin.

If desired, the biologically active substance can be modified or chemically altered to provide reactive groups for attaching, including providing a linking moiety for attachment. There is considerable technology known in the art for such chemical modification or the use of linking moieties, including teaching in such references as U.S. Pat. No. 4,914,210 (issued Apr. 3, 1990 to Levenson et al) and WO-A-89/2932 (published Apr. 6, 1989), both directed to modification of oligonucleotides, U.S. Pat. No. 4,719,182 (issued Jan. 12, 1988 to Burdick et al), Erlanger et al, *J.Biol.Chem.*, 234, 1090 (1959), Wiston et al, *Biochim.Biophys.Acta*, 612, pp.40–49 (1980) and Borzini et al, *J.Immunol.Methods*, 44, pp. 323–332 (1981).

The biologically active substances are attached to particles of the copolymers described herein using activating agents. These activating agents are compounds capable of converting the carboxy groups into an intermediate (such as an ester) which is reactive with the available amine or sulfhydryl groups of the substance.

Useful activating agents include, but are not limited to N-ethyl-5-phenylisoxazolium-3'-sulfonate, chloroformate, the well known water-soluble carbodiimides, as described for example in U.S. Pat. No. 4,181,636 (noted above), dication ethers, carbamoylonium compounds and others readily apparent to one skilled in the art.

Particularly useful water-soluble carbodiimides include, but are not limited to, 1-cyclohexyl-3-[2-morpholinyl-(4)-ethyl]-carbodiimide metho-p-toluenesulfonate and 1-(3-dimethylaminopropyl)-3-ethylcarbodiimide hydrochloride.

Other useful activating agents are dication ethers such as those described in copending U.S. Ser. No. 389,390 (noted above). Included among such compounds are bis(tetramethylformamidinium) ether ditriflate and bis(1-methyl 2-pyridinium) ether ditriflate.

Preferred activating agents are the carbamoylonium compounds described in considerable detail in EP-A-0 308 235 (noted above). Useful carbamoylonium compounds include, but are not limited to, 1-(4-morpholinocarbonyl)-4-(2-sulfoethyl)pyridinium hydroxide, inner salt, 1-(1-pyrrolidinylcarbonyl)pyridinium chloride and 1-(4-morpholinocarbonyl)pyridinium chloride. The most preferred compound for making most reagents of this invention is 1-(1-pyrrolidinylcarbonyl) pyridinium chloride.

The procedure for attaching a biologically active substance to polymeric particles to prepare the reagents of this invention is generally as follows.

The general procedure for preparing the reagent of this invention occurs in two steps. The first step involves contacting an aqueous suspension (or latex) of the polymeric particles with an activating agent to produce reactive intermediates (for example, esters or mixed anhydrides) attached to the particles in place of the original carboxy groups. This step is carried out at a suitable pH using acids or buffers that are appropriate. For the carbamoylonium compounds and dication ethers, the pH is generally less than about 6 (preferably from about 3.5 to about 6). For carbodiimides, the pH is generally from about 4.5 to about 7. The amount of activating agent used in the preparation is generally at least about a two-fold excess over the stoichiometric concentration of total carboxyl groups in the polymeric particles, but the optimum amounts are readily determined by routine experimentation using the teaching provided herein and known in the art. For example, for the carbamoylonium compounds of EP-A-0 308 235 (noted above), the molar ratio of the compound to carboxy groups on the particles is from about 1:1 to about 200:1, and preferably from about 100:1 to about 10:1. For preferred carbamoylonium activating agents, such as 1-(1-pyrrolidinylcarbonyl)pyridinium chloride, the molar ratio of compound to carboxyl groups is from about 1:1 to about 200:1, and preferably from about 2:1 to about 100:1. For dication ethers, this ratio is generally from about 10:1 to about 1000:1, and preferably from about 50:1 to about 400:1.

In the reaction mixture, the % solids of particles is generally from about 0.01 to about 10%, and preferably from about 0.1 to about 5%, in preparing the reagent. The amount of biologically active substance is generally designated by a weight ratio of substance to copolymer of from about 0.0005:1 to about 0.5:1, and preferably from about 0.005:1 to about 0.1:1. However, it should be understood that not all of the substance may become covalently bound to the particles. In fact, a minor amount may be adsorbed, and some may not be bound at all. One skilled in the art could readily perform tests to determine the amount of substance bound to the particles.

Mixing of the biologically active substance and particles is carried out at a temperature of from about 20° to about 37° C. for from about 2 to about 30 hours. The length of time will vary with the temperature, activating agent, biologically active substance and the desired coverage. Any suitable buffer can be used, but 2-(N-morpholino)ethanesulfonic acid is preferred.

The details of representative procedures for making various reagents are shown in the Examples below.

It is desired that the biologically active substance be present in the reagent in an amount of from about 0.0025 to about 30%, and preferably from about 0.005 to about 10%, by weight of the polymer particles. As noted above, not all of the substance mixed with the particles may become bound. Hence, usually an excess of substance is mixed with the particles than actually becomes covalently bound.

In one embodiment of this invention, nucleic acid reagents for hybridization or other assays using water-insolubilized nucleic acids can be prepared using carboxylated polymeric particles, including but not limited to the specific carboxylated polymeric particles described above. Thus, the reagents can be prepared from particles composed of a polymer represented by the structure:

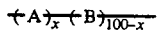

wherein A represents recurring units derived from one or more ethylenically unsaturated polymerizable monomers containing carboxyl groups or salts or precursors of such groups, and B represents recurring units derived from one or more ethylenically unsaturated polymerizable monomers.

Monomers from which A can be derived include, but are not limited to, acrylic and methacrylic acids, itaconic acid, aconitic acid, fumaric acid, maleic acid, β-carboxyethyl acrylate, βcarboxyethyl methacrylate, m & p-carboxymethylstyrene, methacrylamidohexanoic acid and N-(2-carboxy-1,1-dimethylethyl)acrylamide or a salt or anhydride precursor thereof. Monomers from which B can be derived include, but are not limited to, styrene and styrene derivatives (for example vinyltoluene, 4-t-butylstyrene, divinylbenzene and 2-chloromethylstyrene), acrylic and methacrylic acid esters (for example, methyl acrylate, ethyl methacylate, n-butyl acrylate, 2-ethylhexyl methacrylate, methyl methacrylate, 2-hydroxyethyl methacrylate, methacrylamide, ethylene dimethacrylate and 2-hydroxyethyl acrylate), sodium 2-acrylamido-2-methylpropanesulfonate, sodium 3-acryloyloxypropanesulfonate, sodium p-styrenesulfonate, or acrylonitrile. Preferably, B is derived from styrene or a styrene derivative, or an acrylic or methacrylic acid ester.

For both the A and B monomers, it is important that the specific monomers used and their proportions be chosen so as to render the particles water-insoluble.

In the structure identified above, x is from about 0.1 to about 70, and preferably from about 1 to about 20, mole percent.

The preferred monomers from which A is derived are those represented by the structure:

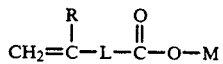

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, as further defined above.

The nucleic acid reagents are advantageously prepared similar to the other reagents described above using an activating agent, but more particularly, the polymeric particles having an average particle size of from about 0.01 to about 20 μm are present in the suspension in an amount of at least about 5% solids, and preferably from about 8% to about 25% solids. The advantage of this feature is that it produces a reagent that gives a much higher signal in an assay for cytomegaloviral DNA. The specific details of the preparation of these reagents is described in Example 15 below.

More generally, however, the method comprises:

A. contacting (1) an aqueous suspension of carboxylated polymeric particles having an average particle size of from about 0.01 to about 20 μm, the particles being present therein at at least about 5% solids with (2) an activating agent to produce reactive intermediate polymer particles having intermediate reactive groups, and B. contacting the reactive intermediate polymer particles produced in step A with an oligonucleotide having a reactive amine or sulfhydryl group which reacts with the intermediate reactive groups to form a covalent linkage between the particles and the oligonucleotide.

Where the oligonucleotide does not have the requisite reactive amine or sulfhydryl groups, they can be added using known procedures and reactants as described for example in U.S. Pat. No. 4,914,210 (issued Apr. 3, 1990 to Levenson et al).

In the analytical or diagnostic methods of this invention, the reagents can be used to detect any specific binding ligand for which there is a receptor molecule. The biologically active substance in a reagent of this invention can be specifically reactive with either the ligand or its receptor. Ligand detection can be carried out in solution or dry form (described below) using test specimens of aqueous fluids (such as biological fluids), or solutions of tissue or cellular materials, and can be quantitative, qualitative or both. In particular, the invention can be used to assay biological fluids of animals, humans or plants, but preferably fluids of humans including whole blood, sera, plasma, lymph, bile, urine, spinal fluid, sputum, lacrimal fluid, perspiration, swab specimens, tissue cultures, stool secretions, cellular fluids, vaginal secretions and semen. It is also possible to assay fluid preparations of human or animal tissue such as skeletal muscle, heart, kidney, lungs, brains, bone marrow or skin.

The ligand can be a drug, hapten, hormone, an antigenic material (lipopolysaccharide or protein) or antibody which has one or more sites for complexation with one or more of the same or different receptor molecules. In immunoassays of this invention, the ligand can be a drug (such as digoxin, phenytoin and carbamazepine), a hormone (such as thyroid stimulating hormone, human chorionic gonadotropin. leutinizing hormone and thyroxine), retroviral component or an antibody to the retrovirus (such as an HIV-I component or its antibody), bacterial infectious agents or components thereof or antibodies thereto (such as Streptococcus A antigen, Chlamydial or Gonococcal antigen or antibody), viruses or components thereof (such as hepatitis, cytomegalovirus or herpes antigen) or antibodies thereto, cancer-producing agents, or C-reactive protein. The ligand can also be biotin or a derivative thereof, and the receptor is avidin or a derivative thereof.

In other embodiments, the ligand can be a nucleic acid (usually in single-stranded form), the amount or presence of which is detected using a complementary single-stranded nucleic acid as the receptor molecule. There are many various assay formats for nucleic acid detection, all of which are readily apparent to one skilled in the art. Detection of HIV-I DNA, $\beta$-globin DNA or cytomegalovirus DNA is of particular interest in the practice of this invention.

In general, a method for the determination of a specific binding ligand comprises:
A. forming a water-insoluble specific binding complex of a specific binding ligand of interest, or a receptor thereof, with a reagent comprising:
   (I) a water-insoluble, nonporous particle as described above, and
   (II) a biologically active substance covalently attached to the particle through the reactive groups, the substance being specifically reactive with either the ligand or a receptor therefor, and
B. detecting the presence of the complex as an indication of the presence or absence of the ligand in the specimen.

In one embodiment, the reagent can be used in competitive binding assays for determination of a specific binding ligand. In general, such an assay comprises:
A. contacting a specimen suspected of containing a water-soluble specific binding ligand with a water-soluble receptor therefor, and with a reagent as described above,
to form a specific binding complex (a) between the receptor and the ligand, and specific binding complex (b) between the receptor and the water-insoluble reagent, and
B. after separating complexes (a) and (b), detecting the presence of either complex as an indication of the presence or amount of the ligand in the specimen.

Such competitive binding assays can be carried out in solution. A solution assay is one in which the reagents are used in a suspension of reagent and test specimen suspected of containing the ligand of interest. Either bound (that is, complexed) or unbound (that is, uncomplexed) materials can be determined in the assay. Physical separation of bound and unbound materials, if desired, can be carried out using any suitable separation technique. In using analytical elements (described below), either vertical or horizontal separation can be used. Bound ligand can be determined using light scattering, turbidimetric, radiometric or spectrophotometric techniques as are known in the art.

In a competitive binding assay, the reagent is generally present in a concentration which depends upon the amount of immunological species (that is, receptor) on the polymeric particles and the ligand of interest. A ligand analog (ligand which is detectably labeled) is also used so there is a competition between ligand and ligand analog for a known amount of receptor available for reaction. The assay is generally carried out by physically contacting and mixing the reagent, ligand analog and test specimen in a suitable container so that complexation occurs. Incubation may be used to promote complexation and any chemical or biological reactions (such as dye formation) needed for detection of the complexes.

More particularly, the ligand is an immunological species and the reaction of ligand and receptor therefor forms an immunological complex which is detectable once water-soluble (uncomplexed) materials are removed from the complex (for example, by filtration or centrifugation) to indicate the presence or absence of the species in the specimen.

The methods of this invention can also be carried out using dry analytical elements. The simplest element can be composed of an absorbent, fluid permeable substrate, for example, a thin sheet of a self-supporting absorbent or bibulous material such as a filter paper or paper strip. This substrate has one or more reaction zones for chemical, biological or specific binding reactions to occur therein. The reagent of this invention is present in at least one of these zones. Other optional zones can include other reagents, such as dyes, dye-providing compounds, scavengers, antioxidants, enzyme substrates or buffers and other materials readily apparent to one skilled in the art. Such elements are known in the art as test strips, analytical elements, slides or dip sticks.

Absorbent materials useful in preparing the elements can include cellulosic materials (such as porous papers), porous polymeric films, mats of glass fibers, woven or nonwoven fabrics and other materials known to one skilled in the art. Preferred substrates are porous spreading layers as described, for example, in U.S. Pat. No. 3,992,158 (issued Nov. 16, 1976 to Przybylowicz et al), U.S. Pat. No. 4,258,001 (issued Mar. 24, 1981 to Pierce et al), U.S. Pat. No. 4,292,272 (issued Sep. 29, 1981 to Kitajima et al) and U.S. Pat. No. 4,430,436 (issued Feb. 7, 1984 to Koyama et al).

Preferred elements can include one or more superposed fluid-permeable layers, all of which are superposed on a nonporous, fluid impermeable support (which can be transparent or not) composed of a suitable polymeric, cellulosic or metallic material. The layers can be used for various purposes, such as for reaction zones, subbing zones, reagent zones, barrier zones, radiation-blocking zones and other uses well known in the art. Where desired, reagents and buffers can move among he layers for the desired reactions to carry out the assay and provide a detectable product and separation of bound and unbound materials. Other components of analytical layers are described, for example, in U.S. Pat. No. 4,042,335 (issued Aug. 16, 1977 to Clément), U.S. Pat. No. 4,132,528 (issued Jan. 2, 1979 to Eikenberry et al), U.S. Pat. No. 4,144,306 (issued Mar. 13, 1979 to Figueras), U.S. Pat. No. 4,670,381 (issued Jun. 2, 1987 to Frickey et al) and EP-A-0 253 581 (published Jan. 2, 1988).

While it is preferred that the reagent of this invention be incorporated into an element for use, this is not critical because the reagent can be added to the element at the time of the assay along with the test specimen. Preferably, however, the ligand analog and reagent of this invention (containing the appropriate receptor) are located within the element in different zones so they will not complex prematurely.

In one preferred embodiment of this invention, an analytical element comprises a nonporous support, having imposed thereon, in order and in fluid contact,
a reagent layer containing one or more reagents for providing a detectable signal in the assay,
a water-soluble layer containing a detectably labeled analog of a ligand of interest, and a porous spreading layer containing the reagent of this invention composed of a receptor (for example, an antibody) for the ligand of interest.

Preferably, the ligand analog is labeled with a enyzme, such as one described below, the ligand is an antigenic material, hormone, hapten or drug, and the receptor is the corresponding antibody. Such elements are particularly useful for the determination of carbamazepine, thyroxine, phenobarbital, phenytoin or digoxin. Most preferably, they are useful for the determination of phenobarbital, phenytoin or digoxin.

A variety of different elements, depending upon the method of assay, can be prepared according to this invention. They can be configured in a variety of forms, including elongated tapes of any desired width, sheets, slides or chips.

The solution or dry assay of this invention can be manual or automated. In general, in the use of dry elements, analyte determination is made by taking the element from a supply roll, chip packet or other source and physically contacting it with a sample of test specimen so the specimen and reagents within the element become mixed in one or more test zones. Such contact can be accomplished in any suitable manner, for example, by dipping or immersing the element into the sample or, preferably, by applying a drop of the specimen to the element with a suitable dispensing means. Wash fluids can also be used in the assay, for example as described in U.S. Pat. No. 4,517,288 (issued May 14, 1985 to Giegel et al).

Assay results are generally determined by observing detectable spectrophotometric changes in the element either visually or with suitable detection equipment.

Another embodiment of this invention is what is known in the art as agglutination assays whereby a ligand is complexed with the reagent of this invention to form a detectable agglutination or clumping of the particles. The resulting agglutination can be detected in a variety of ways, for example visually or with suitable light scattering detection equipment. Representative agglutination techniques are described, for example, in U.S. Pat. No. 4,419,453 (issued Dec. 6, 1983 to Dorman et al), U.S. Pat. No. 4,808,524 (issued Feb. 28, 1989 to Snyder et al), U.S. Pat. No. 4,828,978 (issued May 9, 1989 to Warren III et al) and U.S. Pat. No. 4,847,199 (issued Jul. 11, 1989 to Snyder et al).

Agglutination assays are preferably carried out using reagents of the present invention which are detectably labeled in some manner, such as with a radioisotope in the particle or in the biologically active substance attached thereto, or with a colorimetric or fluorometric dye associated with the particle. Most preferably, a dye is within the interior of the particle, that is away from its surface so as to not interfere with the attachment of a biologically active substance or its complexation. Such particles can be core-shell particles having the dye within a core polymer while the shell copolymer is free of dye. This feature and methods of making such particles are described in more detail in U.S. Pat. No. 4,808,524 (noted above) and in EP-A-0 280 556 (published Aug. 31, 1988). In core-shell polymer particles, the shell copolymer has a composition like that described herein (that is, having the necessary reactive carboxy groups), but the core polymer can be different and need not have reactive groups.

A method for the determination of an immunological species comprises:

A. contacting a specimen suspected of containing an immunological species with a reagent of this invention having a receptor for the species, to form a water-insoluble immunological complex of the species with the receptor, and B. after separating uncomplexed materials from the complex, detecting the presence of the complex as an indicator of the presence or amount of the immunological species in the specimen.

The immunological species can be an antigenic material and the receptor an antibody therefor. Alternatively, the immunological species can be an antibody and the receptor an antigenic material specific therefor. Still again, the immunological species can be an antibody and the receptor an antibody specific therefor.

In still another embodiment, the reagent of this invention can be used in immunometric assays (often called "sandwich" assays). In such assays, the ligand of interest is complexed with two or more receptor molecules (the same or different), one of which is insolubilized or capable of being insolubilized (such as through an avidin-biotin bond), and the other being water-soluble and appropriately labeled (such as with a radioisotope, enzyme, chemiluminescent moiety or other marker known in the art). For example, a sandwich assay for a ligand such as human chorionic gonadotropin (hCG) can be carried out with a reagent of this invention having antibodies to the hormone in combination with enzyme-labeled antibodies to hCG which will complex at different epitopic sites than the reagent antibodies. The resulting sandwich complex is insoluble, detectable and separatable from uncomplexed materials (such as with a microporous filtration membrane). In a preferred embodiment, the reagent of this invention has a receptor for the ligand of interest, and is immobilized on the membrane. Sandwich assays are well known in the art, including GB-A-2,074,727 (published Nov. 4, 1981) and U.S. Pat. No. 4,486,530 (issued Dec. 4, 1984 to David et al), and references noted therein.

Preferably, in the sandwich assays, either prior to, simultaneously with or subsequently to the formation of the water-insoluble complex with the reagent of this invention, the ligand of interest is reacted with a water-soluble specific binding component specifically reactive therefor.

Other ligands which can be detected in sandwich assays according to this invention include, but are not limited to, Streptococcal antigens, antigens extracted from microorganisms associated with periodontal diseases, hepatitis antigens, HIV-I and other retroviral antigens.

In one embodiment of the sandwich assay, the reagent of this invention is directly reacted with the ligand of interest, for example, where the ligand is an antigen, and the reagent comprises antibodies thereto. In another embodiment, however, the reagent is complexed with the ligand indirectly, that is, through an intermediate linking moiety. One example of this is shown in U.S. Pat. No. 4,870,007 (issued Sep. 26, 1989 to Smith-Lewis) where complexation is through an avidin-biotin bond.

Another embodiment of this invention is what is known as a hybridization assay wherein a targeted nucleic acid is detected using complementary probes, one of which is suitably labeled, and the other is immobilized, or capable of being immobilized. The reagent of this invention can be used as an immobilized probe (also known as a capture probe) in such assays. Examples of hybridization assays are shown, for example, in U.S.

Pat. No. 4,358,535 (issued Nov. 9, 1982 to Falkow et al) and U.S. Pat. No. 4,486,539 (issued Dec. 4, 1984 to Ranki et al). These reagents can also be used as capture probes after what is known in the art as polymerase chain reaction amplification, for example, as described in more detail in U.S. Pat. No. 4,683,195 (issued Jul. 28, 1987 to Mullis et al), U.S. Pat. No. 4,683,202 (issued Jul. 28, 1987 to Mullis) and U.S. Ser. No. 273,779 (filed Nov. 21, 1988 by Burdick et al). An amplified nucleic acid is immobilized by hydridization with the reagent of this invention.

In particular, a method for the detection of a nucleic acid comprises:

A. forming a water-insoluble hybridization product between a nucleic acid of interest, with a reagent of this invention having an oligonucleotide covalently attached to the particle through the reactive carboxy group or salt thereof, the oligonucleotide being substantially complementary to the nucleic acid of interest, and B. detecting the presence of the hybridization product as an indication of the presence or amount of the nucleic acid of interest.

In preferred hybridization assays, the nucleic acid of interest is amplified using polymerase chain reaction (known in the art) with suitable reagents (for example, DNA polymerase, dNTPs, primers) prior to capture with the reagent of this invention. HIV-I DNA, cytomegaloviral DNA and $\beta$-globin DNA are readily detected using amplification and detection according to this invention. In one embodiment, one of the primers is biotinylated, and detection of the amplified nucleic acid is accomplished using a conjugate of avidin and an enzyme. The hybridized product can be captured using the reagent which may be attached to or localized on a substrate of some type, including a microporous substrate such as a membrane, or a compartment of a self-contained reaction pouch.

The analytical, sandwich and hybridization assays of this invention can be carried out using suitable equipment and procedures whereby complexed or hybridized product is captured or separated from uncomplexed materials by filtration, centrifugation or other means. Preferably, such assays are carried out using disposable test devices which contain microporous filtration membranes (for example those commercially available from Pall Corp.). Representative test devices are shown in U.S. Pat. No. 3,825,410 (issued Jul. 23, 1974 to Bagshawe), U.S. Pat. No. 3,970,429 (issued Jul. 20, 1976 to Updike) and U.S. Pat. No. 4,446,232 (issued May 1, 1984 to Liotta). Particularly useful test devices are shown in U.S. Ser. No. 98,248 (filed Sep. 18, 1987 by Hinckley et al now abandoned), and are commercially available as Surecel TM test devices (Eastman Kodak Co.).

The analytical separation method of this invention can be used to isolate one or more analytes of interest from a mixture of biological materials. Thus, the reagent of this invention (or several reagents having different substances attached to particles) is generally placed in a column through which a fluid containing the mixture of biological materials is poured, allowing the reagent to extract from the fluid those materials one wants to isolate. This may be useful in the purification of nucleic acids, enzymes, carbohydrates, proteins, lipids, vitamins, steroids, antibodies, peptides or hormones. This procedure is also known as affinity chromatography.

Affinity chromatography can also be used to concentrate dilute solutions of proteins in order to remove denatured forms thereof from refined proteins, and in the separation and resolution of protein and peptide components which have originated in specific chemical modifications.

Another use of this method is to purify nucleic acids, such as those resulting from polymerase chain reaction amplification, as described, for example in U.S. Ser. No. 475,068 (filed Feb. 5, 1990 by Oakes et al) as a CIP of U.S. Ser. No. 325,311 (filed Mar. 17, 1989 by Oakes et al now abandoned).

The reagent of this invention can be supplied for any of the described methods as a single material, or it can be supplied in an analytical element as described above, or yet again in combination with other reagents, test devices and equipment in a diagnostic test kit. For the purification method, the reagent can also be supplied in an affinity chromatography column.

Specifically, a kit for a hybridization assay includes a reagent of this invention having an oligonucleotide complementary to the nucleic acid of interest, and one or more other reagents (for example, labeled probe or polymerase chain reaction reagents), solutions (such as wash or extraction solutions) or articles (such as pipettes, filters, test devices or test vessels) needed for the assay.

In another embodiment, a kit useful for determination of a ligand (for example immunoassay, sandwich assay, diagnostic test or competitive binding assay) includes the reagent of this invention, and one or more other reagents, solutions or articles needed for such an assay (such as ligand analog, labeled receptor, dye-providing compositions, substrates, wash solutions, filters, test devices, extraction reagents and others known in the art).

In the analytical purification method of this invention, the reagent in the chromatography column captures one or more of the substances in the mixture of substances poured through the column.

In one embodiment, the predetermined substances are captured by the reagent, the original eluent is discarded and the captured substances are removed from the column using a solvent which alters the binding characteristics of the substances so they can be uncomplexed. Such solvents include buffers which alter the pH, salt solutions which alter the ionic nature of the complex or solutions containing a second species which will specifically bind to the reagent and replace the captured substance.

Alternatively, the predetermined substances captured by the reagent are discarded, and other chemical or biological materials remaining in the original eluent are collected.

The following examples are for illustrative purposes only, and not to limit the scope of the invention. All percentages are by weight, unless otherwise specified.

EXAMPLE 1

Reagents Having Labeled Bovine Gamma Globulin

This example illustrates the preparation of several reagents of this invention having a radio-labeled protein attached to the polymeric particles. Two different activating agents were used to prepare the reagents. The reagents were compared to a Control reagent similarly prepared using a copolymer outside the scope of this invention.

Copolymers prepared according to the procedures described in copending U.S. Ser. No. 539,768 (of Ponticello and Sutton, noted above) were used in this example. The copolymers were:

Test A: Poly(styrene-co-mono-2-methacryloyloxyethyl glutarate) (97.84:2.16 molar ratio), Test B: Poly(styrene-co-mono-m & p-vinylbenzyl glutarate) (97.8:2.2 molar ratio), Test C: Poly[styrene-co-monomethacryloylpenta(oxyethylene) glutarate] (98.7:1.3 molar ratio), Control Poly(styrene-co-acrylic acid) (95:5 molar ratio).

The protein was attached to the carboxy groups of these polymers using either of the carbamoylonium compounds: (a) 1-(4-morpholinocarbonyl)-4-(2-sulfoethyl)pyridinium hydroxide, inner salt, or (b) 1-(1-pyrrolidinylcarbonyl)pyridinium chloride as activating agents. All polymers were treated under the same conditions. The final dispersions comprised 1% of $^3$H bovine gamma globulin per gram of polymeric particles, 0.3 mg of protein per 30 mg dry weight of particles in 2-(4-morpholino)ethanesulfonic acid buffer (0.1 molar, pH 5.5. The amount of activating agent was 16.6 mg of (a) or 9.6 mg of (b) per tube.

These dispersions were prepared by putting the suspensions of particles (30 mg dry weight) in large microfuge tubes, and each was brought to a volume of 1.5 ml using the noted buffer. The resulting suspensions were centrifuged for 15 minutes at 14,000 rpm and the supernatant discarded. Buffer (1 ml, 0.1 molar) was added, followed by addition of a solution (300 μl) of the activating agent to each tube. The solution of activating agent (a) was prepared by dissolving 199 mg in 3.6 ml of 0.1 molar buffer, and the solution of activating agent (b) was prepared by dissolving 115 mg in 3.6 ml of 0.1 molar buffer. The tubes were then capped and rotated end-over-end at room temperature for 10 minutes. A solution (30 μl) of the labeled protein (10 mg/ml) was added to each tube followed by rotation end-over-end for 4 hours at room temperature.

Reaction of the protein with the carboxy groups on the particles was quenched by the addition of bovine serum albumin (250 μl, 100 mg protein/ml) to each tube. The tubes were then rotated again for an additional 16 hours at room temperature, and each reaction mixture (250 μl) was removed to determine the total labeled protein.

A sample (500 μl) of each reaction mixture was also removed and treated with buffer (400 μl, 0.1 molar) and sodium dodecyl sulfate (100 μl of a 10% solution in deionized distilled water). The resulting mixtures were mixed by tumbling at 37° C. for 16 hours on a rotating disc mounted at a 45° angle (the treatment with surfactant removed adsorbed, but not covalently bound, protein from the particles). The reaction mixtures were centrifuged, and aliquots (500 μl each) were removed to determine the amount of free labeled protein.

The total of $^3$H bovine gamma globulin bound to the particles, the amount of $^3$H bovine gamma globulin covalently bound to the particles and the covalent/total bound ratio are shown in the following Table I. The results show that the reagents prepared according to this invention acceptably bind antibody for use in immunoassays.

TABLE I

| Test | Activation Agent | Total % Bound | Covalent % Bound | Ratio |
|---|---|---|---|---|
| A | a | 97 | 96 | 99 |
|   | b | 91 | 89 | 98 |

TABLE I-continued

| Test | Activation Agent | Total % Bound | Covalent % Bound | Ratio |
|---|---|---|---|---|
| B | a | 97 | 97 | 100 |
|   | b | 94 | 93 | 99 |
| C | a | 90 | 90 | 100 |
|   | b | 49 | 48 | 100 |
| Control | a | 97 | 97 | 100 |
|   | b | 95 | 94 | 99 |

EXAMPLE 2

Reagent Having Anti-Thyroxine Antibodies

This example illustrates the preparation of a reagent of this invention having antibody molecules to thyroxine covalently attached to polymeric particles.

The procedure described in Example 1 was used to attach monoclonal anti-thyroxine antibodies (available from Cambridge/Ventrex Laboratories. Inc.) to the same copolymers, except that the antibody solution (130 μl, 2.3 mg protein/ml) was used in place of labeled bovine gamma globulin. Both activating agents (a) and (b) were used to prepare the reagents. The reaction was quenched, the reaction mixtures were centrifuged, the supernatants decanted, and the particles resuspended in phosphate buffered saline solution (1 ml, pH 7.4). This step was repeated four times, and during the last time, the solids were resuspended in phosphate buffered saline solution (1.8 ml) and merthiolate preservative (0.02%) was added.

The relative amounts of active antibody in the resulting dispersions were determined in an assay in which serial dilutions of the reagent dispersions were mixed with a fixed concentration of an enzyme-labeled analog of thyroxine and alkaline phosphatase (prepared as described by Ito et al in Clin.Chem., 30(10), pp. 1682-1685, 1984). The dilutions were incubated for about one hour with constant agitation at room temperature in phosphate buffered saline solution containing bovine serum albumin (1%). The amount of labeled analog remaining in solution after centrifugation was determined, and the concentration of thyroxine binding sites required to bind 50% of the analog was calculated. The results are summarized as follows in Table II. These data show that the reagents of this invention bind the labeled analog at considerably lower (3-5 times) concentration than the Control reagent using either activating agent.

TABLE II

|  | Theoretical Thyroxine Binding Sites Where 50% of Label is Bound (nmolar) | |
|---|---|---|
|  | Agent (a) | Agent (b) |
| Test A | 20 | 10 |
| Test B | 23 | 13 |
| Test C | 36 | 16 |
| Control | 100 | 56 |

EXAMPLE 3

Reagent Having Oligonucleotide Convalently Bound to Particles

This example illustrates the preparation of a reagent of this invention having an oligonucleotide (or nucleic acid) which is complementary to a nucleic acid of interest.

A sample (50 mg, 0.379 ml of 13.18% suspension) of poly(styrene-co-mono-m & p-vinylbenzyl glutarate) (97.8:2.2 molar ratio) particles was added to 2-(4-morpholino)ethanesulfonic acid buffer (5 ml, 0.1 molar, pH 6). The resulting suspension was centrifuged at 3200 rpm to pelletize the polymer particles. After the supernatant was decanted, the particles were resuspended in buffer (5 ml) in a centrifuge tube. Added to this was the activating agent, N-[3-(dimethylamino)propyl]-N'-ethylcarbodiimide hydrochloride (18.8 mg), followed by an oligonucleotide (0.625 optical density, 1.875 nmole) having the following sequence complementary to β-globin DNA:

wherein A, C, G, and T are the standard representations for adenine, cytosine, guanine and thymine bases in the nucleic acid sequence, and X represents a tetraethylene glycol amine linker having the structure:

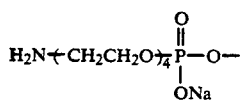

and attached according to the teaching of U.S. Pat. No. 4,914,210 (noted above). The tube was capped and rotated end-over-end for 18 hours at room temperature.

The suspension was then centrifuged at 3200 rpm, the supernatant decanted, and the solids resuspended in glycine (0.1 molar, pH 8.5) containing merthiolate (0.01%). This wash procedure was repeated twice. The final suspension contained 0.87% solids of reagent as determined using spectrophotometric light scattering.

EXAMPLE 4

Reagent Having Antibodies to Human Chorionic Gonadotropin

This example is similar to Example 2. It illustrates the preparation of a reagent useful in an immunoassay.

A sample (10 mg, 65.8 μl of a 15.2% suspension) of polymeric particles as described in Example 3 was added to 2-(4-morpholino)ethanesulronic acid buffer (1 ml, 0.1 molar, pH 6). The resulting suspension was centrifuged at 3200 rpm to pelletize the polymer particles. After the supernatant was decanted, the particles were resuspended in buffer (1 ml) in a centrifuge tube. Added to this was the activating agent, N-[3-(dimethylamino)-propyl]-N'-ethylcarbodiimide hydrochloride (3.76 mg). The tube was capped and rotated end-over-end for 10 minutes at room temperature. Affinity purified goat antibodies to the beta subunit of human chorionic gonadotropin (hCG) (0.123 mg, OEM Concepts, Toms River, N.J.) were added to the tube, and it was rotated again for 18 hours. The suspension was centrifuged at 3200 rpm, the supernatant discarded, and the pellet resuspended in glycine (0.1 molar, pH 8.5) containing merthiolate (0.01%). This procedure was repeated twice to provide a reagent of this invention having antibodies covalently attached to the particles.

EXAMPLES 5-7

Reagents Having Antibodies to Phenobarbital, Phenytoin and Digoxin

These examples illustrate the preparation of reagents of this invention which are useful in both solution and dry competitive binding assays.

Suspensions of polymeric particles used in Example 1 were used [Tests A-C and the Control (except the Control polymer particles had a 96.65:3.35 molar ratio)]. The activating agent used was 1-(1-pyrrolidinylcarbonyl)pyridinium chloride. All particles were treated similarly. The final dispersions comprised antibody (anti-phenytoin for Example 5, anti-phenobarbital for Example 6 and anti-digoxin for Example 7), 0.3 mg of protein per 30 mg dry weight of particles in 2-(4-morpholino)ethanesulfonic acid buffer (0.1 molar, pH 5.5, and activating agent (1.5 mmole agent/g particles, that is 0.045 mmole).

These dispersions were prepared by putting suspensions of particles (30 mg dry weight) in large microfuge tubes, and each was brought to a volume of 1.5 ml using the noted buffer. The resulting suspensions were centrifuged for 15 minutes at 13,000 rpm and the supernatants discarded. Buffer (1 ml, 0.1 molar) was added to each tube, followed by addition of the activating agent (0.3 ml of a solution at 0.15 molar in buffer). The tubes were then capped and rotated end-over-end at room temperature for 10 minutes. A solution of the antibodies was added to the respective tubes: 0.07 ml of anti-phenytoin (4.3 mg/ml), 0.115 ml of anti-phenobarbital (2.6 mg/ml) and 0.196 ml of anti-digoxin (1.53 mg/ml), 0.3 mg total antibody for each, followed by rotation end-over-end for 4 hours at room temperature.

Reactions of the antibodies with the activated particles was quenched by the addition of bovine serum albumin (300 μl, 100 mg protein/ml) to each tube. The tubes were then rotated again for an additional 16 hours at room temperature, centrifuged and supernatants removed for later ELISA analysis, the particles resuspended in phosphate buffered saline solution (1 ml, pH 7.4). This step was repeated three times, and the final resuspension was in phosphate buffered saline solution (1.8 ml) containing merthiolate (0.02%).

The supernatants from the reaction mixtures were analyzed for total antibody concentration by ELISA. The amount of antibody covalently bound to the particles was calculated from the ELISA results.

The relative amounts of active antibody in the preparations were determined in an assay in which serial dilutions of the reagents were mixed with fixed concentrations of the conjugates: alkaline phosphatase-labeled phenytoin, alkaline phosphatase-labeled phenobarbital or horseradish peroxidase-labeled digoxin, all of which were prepared using known procedures as described by Erlanger et al, *J.Biol.Chem.*, 234, 1090 (1959). The reaction between the diluted reagent dispersions and the enzyme-labeled analogs were incubated for one hour at room temperature with constant agitation in phosphate buffered saline solution containing 0.1 or 1% bovine serum albumin. The amount of enzyme-labeled analog remaining in the supernatants after centrifugation was determined, and the concentration of antibody-binding sites required to bind 50% of the enzyme labeled analog was calculated. The results are summarized as follows in Table III:

TABLE III

| Test | Theoretical Binding Sites for Binding 50% of Labeled Analog (nmolar) | | |
|---|---|---|---|
| | Phenytoin | Phenobarbital | Digoxin |
| Example 5 | 4.5 | 6.0 | 0.83 |
| Example 6 | 5.1 | 7.1 | 0.53 |
| Example 7 | 7.0 | 6.0 | 6.3 |
| Control | 6.3 | 10.0 | 5.2 |

The results indicate that each of the reagents of Examples 5 and 6 has higher activity than the same antibody immobilized as part of the Control because they required less reagent for binding 50% of the binding sites. In Example 7, the phenobarbital reagent exhibited better activity than the Control, but the other two reagents had slightly less activity than the Control.

EXAMPLES 8-9

Reagents Having Iodinated Proteins

These examples show the preparation of reagents of this invention having iodinated bovine gamma globulin covalently attached to polymeric particles.

All particles were treated similarly, the final reaction dispersions contained $^{125}I$-bovine gamma globulin (0.3 mg), polymeric particles (30 mg dry weight), 1-(1-pyrrolidinylcarbonyl)pyridinium chloride activating agent (0.5 mmole/g particles) in 2-(4-morpholino)ethanesulfonic acid buffer (0.1 molar, pH 5.5).

The polymeric particles used were those identified as Test B (Example 8), Test C (Example 9) and the Control of Example 1 above. Aliquots of the particle dispersions were placed in 2 ml microfuge tubes and buffer (0.1 molar) added to a total volume of 1.5 ml. The dispersions were centrifuged 10 minutes at 13,000 rpm and the supernatants discarded. The beads were redispersed in the buffer (1 ml) and the activating agent (0.3 ml, 0.15 molar). The tubes were capped and rotated end-over-end for 10 minutes. A solution of the iodinated protein was added to provide 0.3 mg total in each tube, and one set of the reaction mixtures were rotated end-over-end at room temperature for 6 hours, while the other set was rotated end-over end at room temperature for 52 hours. The reaction mixtures were centrifuged and the supernatants removed and analyzed for radioactivity. The resulting reagents were resuspended in phosphate buffered saline solution (1 ml), centrifuged, resuspended in sodium dodecyl sulfate (1%), and analyzed for radioactivity to determine the total amount of iodinated protein bound to the particles.

The particles were then incubated for 16 hours in sodium dodecyl sulfate (1%) at room temperature while tumbling end-over-end to removed adsorbed protein, but leaving covalently bound protein attached. The reagents were pelletized, the supernatants removed and analyzed for radioactivity, then resuspended in sodium dodecyl sulfate (1%). The reagents were centrifuged again, the supernatants discarded, and the reagents analyzed for radioactivity.

The percent of iodinated protein covalently bound to the particles for each reagent are noted as follows in Table IV.

TABLE IV

| Test | % Covalently Bound | |
|---|---|---|
| | 6 hours | 52 hours |
| Example 8 | 96 | 100 |
| Example 9 | 45 | 100 |
| Control | 80 | 100 |

These results indicate that the polymeric particles used in Example 8 react more quickly with the protein than do the Control particles so that a shorter time is needed for complete reaction of protein with the particles. This represents a manufacturing advantage. It also represents an advantage in that antibodies which may be sensitive to the conditions needed for attachment will less likely be deactivated by those conditions due to the shorter reaction times. After 6 hours of reaction, the particles of Example 9 do not provide results as good as the Control, but this example demonstrates that it is still a useful reagent. Longer times for reaction of protein with the particle carboxy groups results in complete attachment for all the particles. This indicates that different polymers and proteins may require various reaction conditions to prepare desired reagents, as one skilled in the art would readily understand.

EXAMPLE 10

Preparation of Reagents Having Oligonucleotides for Cytomegalovirus DNA

This example demonstrates the preparation of reagents having an oligonucleotide covalently attached to carboxy-containing copolymers as described herein. The oligonucleotide is directed to a nucleic acid sequence of cytomegalovirus DNA. The oligonucleotide used herein was synthesized using a Biosearch 8650 DNA synthesizer by the phosphoramidite method described in U.S. Pat. No. 4,725,677 (issued Feb. 16, 1988 to Koster et al) with some modifications in activator (Activator Gold available from Beckman), an additional aqueous wash step (before oxidation) and 1 methylimidazole as a capping reagent in place of 4-(N,N-dimethylamino)pyridine. The reagents used for derivatizing the oligonucleotide for adding linkers and spacers are described in U.S. Pat. No. 4,914,210 (noted above). The oligonucleotide reagents were designed with either (1) a single amino linker at the 3'-end (identified as LB09), or (2) with an amino linker and two tetraethylene glycol spacers at the 3'-end (identified as LB08). The oligonucleotide sequence is as follows using standard base identification (A, C, G, and T):

5'-TCACCCCCAG AGTCCCCTGT ACCC-X-3' wherein, for LB08, X represents an amine linker connected to two tetraethylene glycol spacer units, and, for LB09, X represents the same amine linker without spacer units having the structure:

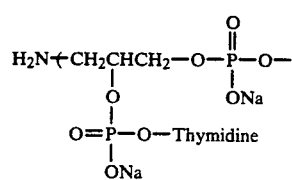

The 5'-end of the purified, deblocked oligonucleotides were labeled with $^{32}P$ by kinasing with $\delta^{32}P$-ATP. LB08 and LB09 [2.0 OD (260 nm) units of each in 20 $\mu l$]

were labeled and used directly in the tests. The LB08 and LB09 oligonucleotides (2 μl) were added to activated bead samples as indicated herein.

The polymeric particles used in this example were as follows:

Polymer A: Poly(styrene-co-mono-2-methacryloyloxyethyl glutarate) (97.8:2.2 molar ratio).

Polymer B: Poly[styrene-co-mono-m & p-(60:40) vinylbenzyl glutarate] 97.7:2.2 molar ratio).

Polymer C: Poly[styrene-co-monomethacryloylpenta(oxyethylene)glutarate] (98.7:1.3 molar ratio).

Polymer D: Poly[styrene-co-monomethacryloyldeca(oxyethylene) glutarate] (98.3:1.7 molar ratio).

Polymer E: Poly[styrene-co-mono-2-(m & p(60:40)vinylbenzylthio)ethyl glutarate] (98.3:1.7 molar ratio).

Polymer F: Poly(styrene-co-mono-p-vinylbenzyl glutarate) (97.2:2.2 molar ratio).

Polymer G: poly[styrene-co-mono-2-(p-vinylbenzylthio)ethyl glutarate] (98.3:1.7 molar ratio).

Polymer H: Poly[styrene-co-3-(p-vinylbenzylthio)propionic acid] (97.6:2.4 molar ratio).

Control A: Poly(styrene-co-acrylic acid) (97.5:2.5 molar ratio).

Control B: Poly(styrene-co-3-acrylamido-3-methylbutanoic acid) (96.9:3.1 molar ratio).

The particles were provided as aqueous latex dispersions having the % solids indicated in the Table V below. Attachment of the oligonucleotides was accomplished by using either of two activating agents: (a) N-(3-(N,N-dimethylamino)propyl)-N'-ethylcarbodiimide hydrochloride (either 100 μl of a 170 mg/1.35 ml solution for Tests 1-6 or 100 μl of a 538 mg/ml solution for Tests 7-16), and (b) 1-(1-pyrrolidinylcarbonyl)-pyridinium chloride (100 μl of 538 mg/ml solution). The activating agent was added to a sample of each dispersion and allowed to react for either 10 minutes (Tests 1-6) or 25 minutes (Tests 7-16).

The resulting activated polymeric particles were then treated with either labeled oligonucleotide (LB08 or LB09, 2.0 μl), and Tests 1-6 were allowed to react for one hour after mixing while Tests 7-16 were allowed to react for 2.5 hours after mixing. The bound oligonucleotides were then separated by centrifugation (2 minutes), and the supernatants were decanted for radioactive counting. The resulting reagents were washed with water, resuspended and centrifuged three times. The combined supernatants from each test and the resuspended reagents were then evaluated for radioactivity, and the results are presented in Table V below.

The results indicate that the amount (%) of oligonucleotide covalently bound to the particles is improved for the reagents of this invention as compared to the Control reagents. Some tests showed much more improvement than others, while some reagents showed improvement with certain activating agents and not others. These data would suggest to one skilled in the art how to find a substantially improved reagent for the detection of cytomegalovirus DNA.

TABLE V

| Test | Oligonucleotide | Activating Agent | Copolymer | Bead Size (μm) | % Solids | % Oligonucleotide Covalently Bound |
|---|---|---|---|---|---|---|
| 1 | LB08 | a | Control A | 1.0 | 16.2 | 2.9 |
| 1 | LB09 | a | Control A | 1.0 | 16.2 | 2.1 |
| 2 | LB08 | a | D | 1.2 | 12.0 | 13.2 |
| 2 | LB09 | a | D | 1.2 | 12.0 | 22.3 |
| 3 | LB08 | a | C | 0.95 | 13.2 | 14.3 |
| 3 | LB09 | a | C | 0.95 | 13.2 | 17.3 |
| 4 | LB08 | a | A | 0.99 | 15.2 | 4.4 |
| 4 | LB09 | a | A | 0.99 | 15.2 | 3.3 |
| 5 | LB08 | a | B | 1.3 | 13.2 | 58.6 |
| 5 | LB09 | a | B | 1.3 | 13.2 | 58.8 |
| 6 | LB08 | a | F | 1.5 | 13.6 | 80.4 |
| 6 | LB09 | a | F | 1.5 | 13.6 | 58.5 |
| 7 | LB08 | a | Control A | 0.92 | 16.2 | 51.3 |
| 7 | LB08 | b | Control A | 0.92 | 16.2 | 2.7 |
| 7 | LB09 | a | Control A | 0.92 | 16.2 | 41.8 |
| 7 | LB09 | b | Control A | 0.92 | 16.2 | 1.7 |
| 8 | LB08 | a | B | 1.3 | 13.2 | 45.2 |
| 8 | LB08 | b | B | 1.3 | 13.2 | 12.3 |
| 8 | LB09 | a | B | 1.3 | 13.2 | 40.0 |
| 8 | LB09 | b | B | 1.3 | 13.2 | 10.4 |
| 9 | LB08 | a | F | 1.5 | 13.6 | 33.7 |
| 9 | LB08 | b | F | 1.5 | 13.6 | 5.8 |
| 9 | LB09 | a | F | 1.5 | 13.6 | 25.9 |
| 9 | LB09 | b | F | 1.5 | 13.6 | 4.5 |
| 10 | LB08 | a | A | 1.0 | 15.2 | 20.2 |
| 10 | LB08 | b | A | 1.0 | 15.2 | 3.4 |
| 10 | LB09 | a | A | 1.0 | 15.2 | 2.6 |
| 10 | LB09 | b | A | 1.0 | 15.2 | 13.3 |
| 11 | LB08 | a | C | 0.85 | 13.2 | 11.1 |
| 11 | LB08 | b | C | 0.85 | 13.2 | 2.3 |
| 11 | LB09 | a | C | 0.85 | 13.2 | 6.8 |
| 11 | LB09 | b | C | 0.85 | 13.2 | 1.5 |
| 12 | LB08 | a | D | 1.2 | 12 | 9.4 |
| 12 | LB08 | b | D | 1.2 | 12 | 2.8 |
| 12 | LB09 | a | D | 1.2 | 12 | 5.0 |
| 12 | LB09 | b | D | 1.2 | 12 | 1.6 |
| 13 | LB08 | a | E | 1.5 | 13.6 | 43.4 |
| 13 | LB08 | b | E | 1.5 | 13.6 | 8.7 |
| 13 | LB09 | a | E | 1.5 | 13.6 | 40.6 |
| 13 | LB09 | b | E | 1.5 | 13.6 | 5.8 |
| 14 | LB08 | a | G | 1.1 | 15.6 | 36.6 |
| 14 | LB08 | b | G | 1.1 | 15.6 | 6.1 |

TABLE V-continued

| Test | Oligonucleotide | Activating Agent | Copolymer | Bead Size (μm) | % Solids | % Oligonucleotide Covalently Bound |
|---|---|---|---|---|---|---|
| 14 | LB09 | a | G | 1.1 | 15.6 | 30.5 |
| 14 | LB09 | b | G | 1.1 | 15.6 | 4.9 |
| 15 | LB08 | a | H | 1.4 | 15.8 | 71.6 |
| 15 | LB08 | b | H | 1.4 | 15.8 | 6.5 |
| 15 | LB09 | a | H | 1.4 | 15.8 | 68.9 |
| 15 | LB09 | b | H | 1.4 | 15.8 | 4.4 |
| 16 | LB08 | a | Control B | 1.1 | 12.0 | 13.8 |
| 16 | LB08 | b | Control B | 1.1 | 12.0 | 2.1 |
| 16 | LB09 | a | Control B | 1.1 | 12.0 | 7.2 |
| 16 | LB09 | b | Control B | 1.1 | 12.0 | 0.7 |

EXAMPLE 11

Assay for Human Chorionic Gonadotropin

This example demonstrates the practice of the present invention to detect hCG using a reagent of this invention.

Materials:

Surecell TM disposable test devices were used containing LoProdyne TM microporous membranes (5 μm, Pall Corp.), each coated with Fluorad TM FC 135 nonionic surfactant (3M, 0.05 g/m$^2$).

A reagent of this invention was prepared by covalently attaching affinity purified goat anti-hCG alpha polyclonal antibodies (OEM Concepts, Toms River, N.J.) to particles of poly[styrene-co-3-(p-vinylbenzylthio)propionic acid] (97.6:2.4 molar ratio) using 1-(1-pyrrolidinylcarbonyl)pyridinium chloride as the activating agent. The procedure for attaching the antibodies was as follows:

A suspension of polymeric particles (3% solids) was mixed with the activating agent (0.1 molar) in 2-(4-morpholino)ethanesulfonic acid buffer in a microfuge tube. The tube was capped, and rotated end-over-end at room temperature for 10 minutes. A solution (810 μl) of the polyclonal antibodies (13.2 mg/ml) was added to the tube followed by rotation end over end for 18 hours at room temperature. The resulting reagent had about 99% of theoretical antibody covalently bound to the polymeric particles.

A composition (2 μl) comprising the reagent (0.9%), polyacrylamide (5%), Uvitex TM dye (0.01%) and thimerosal preservative (0.01%) in glycine buffer (0.1 molar, pH 8.5) was deposited on a finite area of the membrane in one of the test wells (designated the sample well).

Goat gamma globulin was covalently bound to the same type of particles using the same procedure and the resulting reagent was deposited onto the membrane in another test well (designated the negative control well). A third test well (designated the positive control well) contained anti-hCG antibodies covalently bound to the same type of particles and hCG antigen prebound to the antibodies.

The test solution contained hCG (50 mI.U./ml) in a solution of phosphate buffered saline solution (150 mmolar sodium chloride, 50 mmolar sodium phosphate, pH 6.2), bovine serum albumin (0.7%) and merthiolate (0.01%).

A conjugate of anti-hCG monoclonal antibodies (Cambridge Medical Diagnostics) and horseradish peroxidase (Miles) was prepared using the procedures described by Yoshitake et al, Eur.J.Biochem., 101, 395 (1979). This conjugate was mixed with Medix Peroxidase Diluent (Medix Biotech, Inc., Foster City, California) containing Lonzaine TM C amphoteric surfactant (0.1%, Lonza Corp.). The final conjugate concentration was 3.38 μg/ml.

A wash solution was prepared from sodium phosphate (0.1 molar, pH 7.2), sodium decyl sulfate (100 mmolar, 2.7%), sodium chloride (0.3 molar) and thimerosal (0.01%).

A dye-providing composition comprised 2-(4-hydroxy-3-methoxyphenyl)-4,5-bis(4-methoxyphenyl)imidazole leuco dye (0.005%), poly(vinyl pyrrolidone) (1%), sodium phosphate buffer (5 mmolar, pH 6.8) diethylenetriaminepentaacetic acid (10 μmolar), 4'-hydroxyacetanilide (2 mmolar) and hydrogen peroxide (10 mmolar).

Assay Procedure:

The test solution (150 μl) containing hCG (50 mI.U./ml) was added to the three test wells of the test device, and the fluids were allowed to drain through the membranes. The buffered composition containing labeled antibody (1 drop, about 40 μl) was added to each test well, and allowed to drain through. The test wells were washed twice (each time with 300 μl) and allowed to drain through. The dye-providing composition (50 μl) was then added to each test well and allowed to drain through. After incubation for less than 1 minute at room temperature, the dye density on the membranes was evaluated against a color chart for dye density with 10 representing the highest density. The areas around the applied compositions in the test wells were evaluated as background. The assay was carried out three times.

The results are provided in the following Table VI as visual dye densities seen in the specific test wells for each of the three tests:

TABLE VI

| Negative Control Well | | Sample Well | | Positive Control Well | |
|---|---|---|---|---|---|
| Test | Background | Test | Background | Test | Background |
| 0 | 0 | 3-4 | 0 | 7 | 0 |
| 0 | 0 | 4 | 0 | 7 | 0 |
| 0 | 0 | 4 | 0 | 7 | 0 |

These data show that in three separate assays, a very low concentration of hCG (50 mI.U.) can be readily detected with zero background using the reagent of this invention.

For comparison, the above example was repeated but using a Control reagent prepared with the polyclonal antibodies covalently attached to particles similarly prepared from poly[styrene-co-m- & p-(2-chloroethylsulfonylmethyl)styrene] (95.5:4.5 molar ratio) (see the teaching in EP-A-0 323 692, published Jul. 12, 1989). The antibodies were attached by mixing a suspension of the Control particles (3% solids) with borate buffer (0.1 molar, pH 8.5) in a microfuge tube. A solution (810 μl) of the polyclonal antibodies (13.2 mg/ml) was added to the tube followed by rotation end-over-end for 18 hours at room temperature. The resulting reagent had about 99% of theoretical antibody covalently bound to the particles.

The test solutions containing hCG, conjugate composition, wash solution and dye-providing composition were the same as described above.

The results of the Control assay using the procedure noted above were found to be as follows: There was less dye formation generated by the low concentration (50 mI.U./ml) of hCG, and negligible background. Because the assay was carried out in less than two minutes, the dye signal for eight separate tests averaged only 1.9, which is considerably lower than the results provided with the present invention (Table VI).

EXAMPLE 12

Reagent and Assay for HIV-I DNA Detection

This example illustrates the preparation of several reagents of this invention having oligonucleotides covalently bound to polymeric particles, and their use in nucleic acid assays to detect either HIV-I DNA, β-globin DNA or both. The methods are carried out using analytical procedures and devices described in more detail in U.S. Ser. No. 306,954 (filed Feb. 3, 1989 by Findlay et al now abandoned) whereby the reagents were immobilized on LoProdyne TM microporous membranes (Pall Corp., 5 μm).

Materials:

The polymers used to prepare reagents for evaluation are as follows:

Control: Poly(styrene-co-acrylic acid) (97.5:2.5 molar ratio).

Polymer A: Poly(styrene-co-mono-m & p(60:40)-vinylbenzyl glutarate) (97.84:2.16 molar ratio).

Polymer B: Poly[styrene-co-3-(p-vinylbenzylthio)propionic acid] (97.59:2.41 molar ratio).

Polymer C: Poly[styrene-co-mono-2-(4-vinylbenzylthio)ethyl succinate] (98.17:1.83 molar ratio).

Polymer D: Poly(styrene-co-mono-4-vinylbenzyl succinate) (97.71:2.29 molar ratio).

These polymers were prepared using the procedures described in more detail in cofiled and copending U.S. Ser. No. 539,768 of Ponticello and Sutton (noted above).

The oligonucleotide used to make the reagent is complementary to a portion of HIV I DNA in the gag region, and has the following nucleic acid sequence:

5'-ATTAAATAAA ATAGTAAGAA T-3' wherein X represents an amino group attached to the oligonucleotide through an ethylene glycol spacer according to U.S. Pat. No. 4,914,210 (noted above).

Suspensions of particles of each polymer were washed with 2-(N-morpholino)ethanesulfonic acid buffer (0.1 molar, pH 6). Samples (30 μg) of particles were suspended in the buffer (1 ml) and mixed with the oligonucleotide (0.0288 ml of 57.3 OD/ml purified water, 1.65 OD units) and 1-(3-dimethylaminopropyl)-3-ethylcarbodiimide hydrochloride (0.15 ml of 100 mg/ml buffer solution). The resulting mixtures were rotated end-over-end at room temperature for 15 hours and centrifuged. The reagents were washed three times with purified water and resuspended in purified water at a 0.9% solids content.

The resulting reagents were deposited on separate LoProdyne TM microporous membranes located in test wells of Surecell TM disposable test devices, in defined regions less than 2 mm² in diameter, and allowed to dry to about 30 minutes at room temperature. The resulting diagnostic test elements were then used in the assays described below.

Primers used in the amplification of HIV-I DNA had the following nucleic acid sequences:

5'-X-TTTGGTCCTT GTCTTATGTC CAGAATGC-3' and

5'-ATAATCCACC TATCCCAGTA GGAGAAAT-3' wherein X represents a biotintetraethylene glycol ester spacer, prepared and attached according to U.S. Pat. No. 4,914,210 (noted above).

Primers used in the amplification of β-globin DNA had the following nucleic acid sequences:

5'-X-CAACTTCATC CACGTTCACC-3' and

5'-ACACAACTGT GTTCACTAGC-3' wherein X represents a biotin amino linked, prepared and attached according to U.S. Pat. No. 4,914,210 (noted above).

All primers and oligonucleotides used in this example (and in all other examples of this application) were prepared using standard phosphoramidite chemistry, purified by high pressure liquid chromatography and characterized by standard sequencing procedures.

DNA polymerase was isolated from *Thermus aquaticus* according to procedures described in U.S. Pat. No. 4,889,818 (issued Dec. 26, 1989 to Gelfand et al) (1 unit corresponds to 10 mmole of dNTP incorporated into the primer extension product in 30 minutes at 37° C.).

A streptavidin-horseradish peroxidase conjugate was obtained from Zymed Labs (San Francisco), and was diluted 1;4000 with a phosphate buffered saline solution containing casein (0.5%), 3-(N-morpholino)propanesulfonic acid buffer (100 mmolar, pH 7.5) and preservative (0.01%). The final conjugate concentration was 312 ng/ml. The phosphate buffered saline solution contained sodium phosphate (25 mmolar, pH 7.3) and sodium chloride (75 mmolar).

A dye-providing composition comprised 2-(4-hydroxy-3-methoxyphenyl)-4,5-bis(4-methoxyphenyl)imidazole leuco dye (0.005%), poly(vinyl pyrrolidone) (1%), sodium phosphate buffer (5 mmolar, pH 6.8) diethylenetriaminepentaacetic acid (10 μmolar). 4'-hydroxyacetanilide (5 mmolar) and hydrogen peroxide (10 mmolar).

Assay:

The procedure for detecting HIV-I was carried out in the following manner.

An HIV-I DNA target was isolated from the HUT cell line, which contains a single integrated copy of the HIV viral genome, obtained from Dr. Bernie Poiesz at Syracuse University.

A β-globin DNA target was isolated from human placental cells obtained from Sigma Chemical Co.

Three target samples were subjected to amplification and detection procedures:

Sample A: Contained HIV-I DNA target, β-globin DNA target and the primers for the HIV-I DNA target only.

Sample B: Contained β-globin DNA target and primers therefor only.

Sample C: Contained both targets and primers for both targets.

Mixtures for polymerase chain reaction to amplify the target HIV-I DNA contained tris(hydroxymethyl)aminomethane buffer (10 mmolar, pH 8), potassium chloride (50 mmolar), magnesium chloride (10 mmolar), gelatin (10 μg), the appropriate primers noted above (100 pmolar of each), dNTP's (1.5 mmolar of each), the DNA polymerase noted above (7.5 units), and target: either β-globin DNA (1 μg) or HIV-I DNA (about $10^{-16}$ molar). The total volume of each mixture was 100 μl.

Each reaction mixture was placed into a polypropylene microcentrifuge tube, primer extension products were formed and amplification of the target nucleic acid was carried out using 30 thermal cycles as follows:

| | |
|---|---|
| 70° C., rising to 95° C. | 1 minute |
| 95° C. | 0.5 minute |
| 95° C., lowering to 55° C. | 1.25 minute |
| 55° C. | 0.5 minute |
| 55° C., rising to 70° C. | 0.75 minute, and |
| 70° C. | 1 minute. |

After amplification, aliquots (5 μl) of each reaction mixture was added to a solution (95 μl) containing tris(hydroxymethyl)aminomethane buffer (10 mmolar, pH 8), potassium chloride (50 mmolar), magnesium chloride (10 mmolar) and gelatin (1 μg/10 ml solution), heat denatured (5 minutes at 95° C.) and added (about 95 μl of each mixture in each test well) to the Surecell ™ test devices described above having reagent immobilized therein.

Each test well was sealed with tape, and the devices were incubated at 42° C. for 5 minutes to hybridize the amplified target HIV-I DNA to the water-insoluble reagent immobilized in the test wells. The sealing tape was removed from each test well, followed by washing with a buffered solution (250 μl) containing phosphate buffer (20 mmolar, pH 7.4), sodium chloride (300 mmolar) and ethylenediaminetetraacetic acid (2 mmolar) at 55° C.

The peroxidase conjugate (50 μl, 15.6 ng) was added to each test well, and the test devices were incubated at room temperature for 2 minutes. A second wash (250 μl) was carried out using the buffered solution noted above. The dye-providing composition (100 μl) was then added to each test well, followed by another incubation at room temperature for 2 minutes. Dye formation was stopped by the addition of sodium azide (100 μl of 0.1% solution), and the resulting red dye in the test wells was visually evaluated. Each assay was duplicated.

The results of dye formation was graded on a scale of 0 to 10 with 10 representing the highest dye density. The results in the following Table VII are duplicate readings for each reagent and sample.

TABLE VII

| | Dye Density | | |
|---|---|---|---|
| Reagent | Sample A (HIV-I DNA Only) | Sample B (β-Globin DNA Only) | Sample C (HIV-I + β-Globin DNA) |
| Control | 2.0, 2.0 | 0.25, 0.25 | 4.0, 2.0 |
| Polymer A | 4.0, 3.0 | 0.25, 0.25 | 5.0, 4.0 |
| Polymer B | 6.0, 5.0 | 0.50, 0.50 | 6.0, 6.5 |
| Control | 2.0, 4.0 | 0, 0 | 3.0, 3.0 |
| Polymer A | 3.0, 5.0 | 0.50, 0.25 | 4.0, 4.0 |
| Polymer C | 7.0, 7.0 | 0.50, 0.25 | 6.0, 7.5 |
| Control | 3.0, 2.0 | 0.5, 0.5 | 4.0, 2.0 |
| Polymer A | 4.0, 4.0 | 0.5, 0.5 | 5.0, 4.0 |
| Polymer D | 7.0, 7.0 | 0.5, 0.5 | 7.0, 6.0 |

These results indicate that the reagent of this invention was successfully used as a probe for the detection of amplified HIV-I DNA. The β-globin DNA target, however, was not detected to an appreciable extend even after its amplification because no capture reagent was used having an oligonucleotide complementary to β-globin DNA. The background dye densities (Sample B) were acceptably low.

EXAMPLE 13

Reagent and Assays for HIV-I DNA and Beta-Globin DNA Detection

This example was carried out similarly to Example 12 except a different oligonucleotide was used in preparing the reagent for HIV-I DNA detection, and β-globin DNA was also detected after amplification of the target nucleic acid using a reagent having an oligonucleotide complementary to β-globin DNA.

The reagent for detecting HIV-I DNA was prepared using an oligonucleotide having the following sequence;

5'-X-ATCCTGGGAT TAAATAAAAT AGTAAGAATG TATAGCCCTA C-3' wherein X is an amino group attached to the oligonucleotide with a spacer using the procedure described in U.S. Pat. No. 4,914,210 (noted above).

The reagent for β-globin DNA detection was prepared using an oligonucleotide having the following sequence:

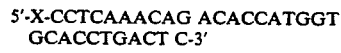

5'-X-CCTCAAACAG ACACCATGGT GCACCTGACT C-3' wherein X is an amino group attached to the oligonucleotide using the procedure described in U.S. Pat. No. 4,914,210 (noted above).

Three target samples were subjected to amplification and detection procedures using the HIV-I DNA reagent and the β-globin DNA reagent:

Sample A: Contained HIV-I DNA target, β-globin DNA target and the primers for the HIV-I DNA target only.

Sample B: Contained β-globin DNA target and primers therefor only.

Sample C: Contained both targets and primers for both targets.

Amplification was carried out as described in Example 12, and the resulting dye densities were evaluated as shown therein. The test results are provided in Table VIII below for each reagent and test sample.

TABLE VIII

| Polymer | Reagent Oligonucleotide* | Dye Density | | |
|---|---|---|---|---|
| | | Sample A (HIV-I DNA Only) | Sample B (β-Globin DNA Only) | Sample C (Both DNA's) |
| A | β-globin DNA | 0, 0 | 9.5, 9.5 | 10, 10 |
| A | HIV-I DNA | 9.0, 9.0 | 0, 0 | 8.5, 8.5 |
| B | HIV-I DNA | 8.0, 8.5 | 0.5, 0.5 | 8.0, 8.0 |
| A | β-globin DNA | 0, 0 | 9.5, 9.5 | 9.5, 10 |
| A | HIV-I DNA | 8.5, 9.0 | 0, 0 | 8.5, 9.0 |
| C | HIV-I DNA | 9.5, 9.5 | 0.5, 0.5 | 9.0, 9.5 |
| A | β-globin DNA | 0, 1.0 | NT , 9.5 | 10, 9.5 |
| A | HIV-I DNA | 9.0, 9.5 | NT , 0.25 | 9.0, 9.0 |
| D | HIV-I DNA | 9.5, 9.5 | NT , 0.25 | 10, 9.5 |

*Oligonucleotide complementary to listed target.
NT: no test because the background density was 5.0. All other backgrounds were less than 1.0.

EXAMPLE 14

Assay for HIV-I DNA in Polymeric Pouch

This example is similar to Example 12 except that HIV-I DNA is detected using a formulated container useful for holding reagents for the assay. The container is similar in construction to that described in copending U.S. Ser. No. 339,923 (filed Apr. 17, 1989 by Schnipelsky et al now abandoned as a CIP of U.S. Ser. No. 306,735, filed Feb. 3, 1989 now abandoned).

Materials:

A container for the assay was prepared from two sheets of Scotchpak 241 TM heat sealable film (3M Corp.) which is a laminate of polyethylene on poly-(ethylene terephthalate). The polyethylene side of the film served as a heat-activated adhesive. A flow channel was formed in one of the sheets by laying it on a mold having a groove therein, heating it at a temperature below the melting point of the polyethylene, and while it was heat relaxed, mechanically stretching the film into the groove to form a channel. The channelled piece was then aligned with a second piece of Scotchpak 241 TM heat sealable film on which a reagent of this invention (described below) was immobilized in a particular region. This alignment was with the polyethylene surfaces of the two films facing each other. The two films were then heat sealed along both side boundaries of the channel so there was no leakage along those sides.

The resulting "detection channel" was used to simulate a "flow-by" assay format. Each detection channel had an inlet port for sample introduction, a reagent of this invention immobilized therein, and an outlet port to allow fluids to exit the channel and to be collected. Fluid reagents were forced into the channel to contact the immobilized reagent before exiting the channel.

The reagents used in this example were prepared using Polymers B, C and D of Example 12, and were prepared using the procedure of that example. The resulting reagents (2 μl of a 0.9% suspension) were deposited on a defined region (about 2 mm diameter) of the detection channel for individual pouches as described above (channel size was about 19 mm by 8 mm) and allowed to dry at room temperature.

The HIV-I DNA target and primers were the same as those used in Example 12. The reaction mixture for polymerase chain reaction was the same except gelatin was present at 0.01% and the primers were present at 1 μmolar each.

Assay:

A solution containing the HIV-I DNA target ($10^{-16}$ molar) was amplified using polymerase chain blisters on a standard thermocycler and the polymerase chain reaction mixture (100 μl) for 30-33 cycles using the protocol:

| incubation at 94° C. | 4 seconds, and |
|---|---|
| incubation at 65° C. | 30 seconds. |

A sample (200 μl) of a 5:95 dilution of the resulting amplified reaction mixture in a buffer solution [containing tris(hydroxymethyl)aminomethane buffer (10 mmolar, pH 8.3), potassium chloride (50 mmolar), magnesium chloride (10 mmolar) and gelatin (0.01%)] was heated in a tube at 95° C. for 5 minutes to denature the double-stranded targets. The heated solution was transferred to a syringe barrel and injected into each detection channel in a manner to insure even coverage of the immobilized reagents in the channels. Each channel was then incubated at 42° C. for 5 minutes to anneal the reagent to the single0stranded HIV-I nucleic acid target. The fluid was removed from the detection channels by forcing the liquid out with air and the fluid was collected with a syringe.

A preheated (55° C.) wash solution was injected into each detection channel. This solution comprised a buffer solution (400 μl) comprising sodium dihydrogen phosphate (10 mmolar, pH 7.4), sodium chloride (150 mmolar), ethylenediaminetetraacetic acid (1 mmolar) and sodium decyl sulfate (1%). The wash solution was removed, and the streptavidin-horseradish peroxidase conjugate of Example 12 (200 μl) was then injected into each detection channel and incubated at room temperature for two minutes. The fluid was removed and a second wash (400 μl) was introduced and removed. The dye-providing composition of Example 12 (200 μl) was then introduced into each channel and incubated at room temperature for 1-2 minutes and removed. Lastly, a solution of sodium azide (200 μl of a 0.1% solution) was introduced to stop dye formation, and removed.

The resulting dye formed in each channel was visually graded on a scale of 0 to 10 with 10 representing the highest dye density. The results of the readings are shown in the following Table IX for the average of three separate tests for each reagent.

TABLE IX

| Reagent | Dye Density |
|---|---|
| Polymer B | 5.2 |
| Polymer C | 5.5 |
| Polymer D | 5.3 |

Similar experiments were carried out successfully wherein the container in which the dye was formed was a self-contained vessel (or pouch) which had compartments for all reagents and solutions needed for the assay, and a separate compartment for the reaction. Such self-contained vessels are described in more detail in U.S. Ser. No. 339,923 (noted above).

EXAMPLE 15

Preparation of Reagents Useful for Detecting Cytomegaloviral DNA

This invention describes a novel method for preparing hybridization reagents which can be used in hybridization or polymerase chain reaction assays. The reagents are useful in the detection of cytomegaloviral DNA.

Materials:

Polymeric particles composed of poly[styrene-co-3-(p-vinylbenzylthio)propionic acid] (97.6:2.4 molar ratio, 1.4 μm average diameter) were used to make the reagents.

The activating agent was 1-(3-dimethylaminopropyl)-3-ethylcarbodiimide hydrochloride, and the buffer was 2-(N-morpholino)ethanesulfonic acid (0.1 molar, pH 6).

The oligonucleotides used have the following sequences, identified using standard notation for the bases:

1  5'-GGTGTCACCC CCAGAGTCCC CTGTACCCGC-3'
2  5'-GACACAGTGT CCTCCCGCTC CTCCTGAGCA-3'
3  5'-GTGGAAGGCG GCTCGCTGGA AGCCGGTCGT-3'
4  5'-GAACCGAGGG CCGGCTCACC TCTATGTTGG-3'

The oligonucleotides were attached to the particles through the 3'-end using the following linking group:

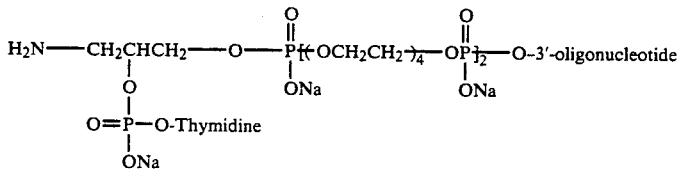

Reagent Preparation

A suspension of the polymeric particles (about 12–16% solids) was centrifuged (5000 rpm) and the resulting pellet was added to 2-(4-morpholino)ethanesulfonic acid buffer (500 μl, 0.1 molar, pH 6), and centrifuged again for about 7 minutes. This procedure was repeated and finally the particles were resuspended in buffer (about 12% solids).

Four tubes containing the noted suspension of particles were prepared by adding the suspension (380 μl) noted above to the buffer (120 μl). A solution (100 μl) of the activating agent (125 mg in 500 μl nanopure water) was added to each tube, and the resulting mixtures were mixed by manual end-over-end rotation for about 5 minutes at room temperature to provide activated polymeric particles.

A solution (2 OD) of each oligonucleotide was added to different tubes in the following volumes: 48.3 μl of #1, 37.7 μl of #2, 45.4 μl of #3 and 32.3 μl of #4. Each tube contained 600 μl of activated particles. The tubes were then rotated end-over-end at room temperature for about 18 hours to covalently bind the oligonucleotides to the activated particles.

The reaction mixtures were then centrifuged and the pellets resuspended in nanopure water (500 μl) and centrifuged again. The treatment with the water and centrifugation was repeated twice more, and the final pellet was resuspended in nanopure water (600 μl) to make a suspension of reagent (about 12% solids). This suspension was diluted to about 1% solids for use in an assay. The concentrations were determined spectrophotometrically by dilution and comparison with a standard dilution curve.

EXAMPLE 16

Assay for Cytomegaloviral DNA

Assay A for cytomegaloviral DNA was carried out using the reagents described above in Example 15 prepared using 12% suspensions of polymeric particles. It was compared to Assay B carried out using the reagents of this invention, but which were prepared using a prior art procedure using about 1–3% suspensions of the polymeric particles.

Materials and Methods:

The target DNA to be detected was a 200 nucleotide segment of the late antigen (LA) region and a 265 nucleotide segment of the Major Immediate Early (MIE) region of the CMV Towne strain (ATCC VR 977).

The oligonucleotides used to detect the LA region had the following sequences:

5'-GTCGAAGGCG GCTCGCTGGA AGCCGGTCGT 3' and

5'-GAACCGAGG CCGGCTCACC TCTATGTTGG-3'.

The primers used for LA region detection had the following sequences:

5'-CACCACGCAG CGGCCCTTGA TGTTT-3' and

5'-GTCGCCTGCG CCAGGTGCTT CG-3'.

The oligonucleotides used to detect the MIE region had the following sequences;

5'-GGTGTCACCC CCAGAGTCCC CTGTACCCGC-3' and

5'-GACACAGTGTCCTCCCGCTC CTCCTGAGCA-3'.

The primers for the MIE region had the following sequences:

5'-CAGCACCATC CTCCTCTTCC TCTGG-3' and

5'-GAGGCTATTG TAGCCTACAC TTTGG-3'.

The oligonucleotides were attached to the polymeric particles as described in Example 15 using about 12% suspensions of the particles to prepare the reagents (or probes) of this invention for Assay A. The oligonucleotides were attached to the polymeric particles using 1-3% suspensions of the particles to prepare reagents (or probes) for Assay B.

The reagents for Assay A for the LA region were mixed (1 μl of a 0.5% suspension of each reagent), and spotted onto a defined area of the membrane (5 μm LoProdyne ™ microporous membrane, Pall Corp.) in the test wells of one set of Surecell ™ test devices (Eastman Kodak Co.). The reagents for Assay A for the MIE region were similarly mixed and spotted onto a second defined area of the same membranes in the same devices. The applied reagents were allowed to dry for about 30 minutes at room temperature.

The reagents for Assay B (prepared using prior art procedures) for the LA region were mixed and spotted as described above in a second set of test devices. The reagents for Assay B for the MIE region were mixed and spotted onto a second defined area of the same membranes.

A streptavidin-horseradish peroxidase conjugate was obtained from Zymed Labs (San Francisco), and was diluted 1:8000 with a phosphate buffered saline solution containing casein (0.5%), 3-(N-morpholino)propanesulfonic acid buffer (100 mmolar, pH 7.5) and preservative (0.01%). The final conjugate concentration was 156 ng/ml. The phosphate buffered saline solution contained sodium phosphate (25 mmolar, pH 7.3) and sodium chloride (75 mmolar).

A dye-providing composition was prepared containing 2-(4-hydroxy-3,5-dimethoxyphenol)-4,5-bis(4-methoxyphenyl)imidazole as follows:

Solid leuco dye (to make a 0.1% solution) was dissolved in a solution of 20% poly(vinylpyrrolidone) in sodium phosphate buffer (5 mmolar). This solution was then added to a solution containing hydrogen peroxide (10 mmolar), 4'-hydroxyacetanilide electron agent (5 mmolar) and diethylenetriaminepentaacetic acid chelating agent (10 μmolar) in sodium phosphate buffer to product a final concentration of 1% poly(vinylpyrrolidone) and 0.005% leuco dye.

DNA polymerase, prepared according to the procedures described in EP-A-0 0258 017 (1 unit corresponds to 10 mmoles of dNTP incorporated into the primer extension product in 30 minutes at 37° C.), was obtained from Cetus Corp.

Assay:

To buffer solutions containing tris(hydroxymethyl)aminomethane buffer (10 mmolar, pH 8), potassium chloride (50 mmolar), magnesium chloride (10 mmolar) and gelatin (10 μg) were added the primers described above (40 pmoles of each), dNTPs (1.5 molar of each) and the polymerase described above (7.5 units). In addition, the Towne strain targets described above were added. The total volume was 100 μl.

Each solution described above was placed into a polypropylene microfuge tube, primer extension products were formed, and amplification promoted using 33 consecutive thermal cycles as follows:

| | |
|---|---|
| 66° C. rising to 92.5° C. | 35 seconds |
| 92.5° C. | 1 minute |
| 92.5° C. lowering to 66° C. | 45 seconds |
| 66° C. | 1 minute |

After amplification, aliquots (5 μl) of each mixture were added to a solution (95 μl) of tris(hydroxymethyl)aminomethane buffer (10 mmolar, pH 8) containing potassium chloride (50 mmolar), magnesium chloride (10 mmolar) and gelatin (1 μg/10 ml solution), heat denatured (5 minutes at 95° C.), then added to the test wells of the Surecell ™ test devices described above (about 95 μl of each solution in individual wells).

The test devices were incubated for 5 minutes at 42° C. to hybridize the amplified DNA target to the respective reagents (or probes) immobilized in the test wells. The hybridized products were washed with a buffered solution (250 μl) containing phosphate buffer (10 mmolar, pH 7.4), sodium chloride (150 mmolar), ethylenediaminetetraacetic acid (1 mmolar) and sodium decyl sulfate (1%) at 55° C.

The peroxidase-labeled avidin conjugate described above (50 μl, 7.8 ng) was added to each test well, and the devices were incubated at room temperature for 2 minutes. A second wash (250 μl) was carried out using the buffered solution noted above. The leuco dye solution (100 μl) was added to each test well followed by another incubation at room temperature for 2 minutes. The formation of dye was quenched by the addition of sodium azide (100 μl of 0.1% solution), and the resulting dye signals were evaluated on the membranes.

The amount of dye in each test device was visually evaluated against a color scale having values of 0 to 10 with 10 representing the highest dye density. The results are shown in Table X below for four separate tests for each of Assays A and B.

TABLE X

| | Dye Density Readings | | | |
|---|---|---|---|---|
| | LA Region | | MIE Region | |
| | Assay A | Assay B | Assay A | Assay B |
| Test 1 | 7.5 | 3 | 8 | 5.5 |
| Test 2 | 7.25 | 2.5 | 8 | 5 |
| Test 3 | 7 | 2.25 | 8 | 8 |
| Test 4 | 7.25 | 2.5 | 8 | 5 |

EXAMPLE 17

Comparative Example of Reagents

This example illustrates the preparation of several reagents of this invention and their comparison with reagents prepared using polymers outside the scope of this invention.

The particles used to prepare the reagents were composed of the following copolymers:

Test A: Poly(styrene-co-mono-m & p-vinylbenzyl glutarate) (97.84:2.16 molar ratio), Test B: Poly(styrene-co-mono-p-vinylbenzyl glutarate-co-divinylbenzene) (97.01:2.16:0.83 molar ratio), Test C: Poly(styrene-co-mono-2-methacryloylo xyethyl glutarate) (97.84:2.16 molar ratio), Test D: Poly(styrene-co-mono-2-methacryloylo xyethyl glutarate-co-divinylbenzene) (97.01:2.16:0.83 molar ratio), Test E: Poly[styrene-co-monomethacryloylpenta(oxyethylene) glutarate] (98.7:1.3 molar ratio), Test F: Poly[styrene-co-monomethacryloyldeca(oxyethylene) glutarate] (99.2:0.8 molar ratio), Test G: Poly[styrene-co-mono-2-(m & p-vinylbenzylthio)ethyl glutarate] (98.3:1.7 molar ratio), Test H: Poly[styrene-co-mono-2-(p-vinylbenzylthio)ethyl glutarate] (98.25:1.75 molar ratio), Test I: Poly[styrene-co-3-(p-vinylbenzylthio)propionic acid] (97.59:2.41 molar ratio), Test J: Poly[styrene-co-mono-2-(4-vinylbenzylthio)ethyl succinate] (98.17:1.83 molar ratio), Test K: Poly{styrene-co-4-[2-(carboxymetho xyacetoxy)ethylthiomethyl]styrene} (98.26:1.74 molar ratio), Test L: Poly(styrene-co-mono-4-vinylbenzyl succinate) (97.71:2.29 molar ratio), Test M: Poly[styrene-co-mono-methacryloylpenta(oxyethylene) phthalate] (98.81:1.19 molar ratio), Control A: Poly(styrene-co-acrylic acid) (95:5 molar ratio), and Control B: Poly(styrene-co-3-acrylamido-3-methylbutanoic acid) (96.9:3.1 molar ratio).

Proteins were attached to the polymeric particles using 1-(1-pyrrolidinylcarbonyl)pyridinium chloride as the activating agent. All particles were treated under the same conditions. The final dispersions comprised antibody (either tritiated bovine gamma globulin as in Example 1 above, or thyroxine antibodies as in Example 2 above) in an amount of 1.7 mg/m$^2$ of polymer surface area in 2-(4-morpholino)ethanesulfonic acid buffer (0.1 molar, pH 5.5) and activating agent (1.5 mmole agent/g particles or 0.045 mmole).

These dispersions were prepared by adding suspensions of the particles (30 mg dry weight) to large microfuge tubes, and each was brought to a volume of 1.5 ml using the noted buffer. The resulting suspensions were centrifuged for 15 minutes at 13,000 rpm and the supernatants discarded. Buffer (1 ml, 0.1 molar) was added to each tube, followed by addition of the activating agent (0.3 ml of a solution at 0.15 molar in buffer). The tubes were then capped and rotated end-over-end at room temperature for 10 minutes to provide activated polymeric particles.

A solution of the respective protein was added to respective tubes containing activated polymeric particles to provide a final concentration of 1.7 mg/m$^2$ of polymer particles. Tritiated bovine gamma globulin was added to certain tubes while thyroxine monoclonal antibodies (Cambridge/Ventrex) were added to other tubes. Buffer was then added to all tubes to achieve a final volume of 1.5 ml. The tubes were rotated end-over-end at room temperature for 24 hours to react the protein with the activated particles.

Reaction of antibodies with particles was quenched by the addition of bovine serum albumin (250 μl, 100 mg protein/ml) to each tube. The tubes were then rotated again for an additional 16 hours at room temperature.

The reagents having attached $^3$H bovine gamma globulin were treated as described in Example 1 to determine the total amount of protein attached as well as the amount covalently bound.

The reagents having thyroxine antibodies attached were washed and the relative amounts of active antibody in the resulting dispersions were determined as described in Example 2.

The results are summarized in Table XI below. The results indicate that the tritiated bovine gamma globulin was covalently bound very well in most of the reagents of this invention. Reagents of Tests E and F did not covalently bind the protein as well as the other reagents. However, when an aromatic carboxy functional group was added to the end of the linking group (as for the reagent in Test M), the amount of covalently bound protein was increased substantially.

The reagents having bound antibodies showed 3–20 times more activity than the reagents in the Controls, as indicated in the last column of Table XI.

TABLE XI

| Test | Total % Bound | % Covalent Bound | Covalent: Total Ratio | Theoretical Thyroxine Binding Sites where 50% of Label is Bound (nmolar) |
|---|---|---|---|---|
| A | 97 | 96 | 0.99 | 2.4 |
| B | 96 | 95 | 0.99 | 3.2 |
| C | 96 | 96 | 1.0 | 2.6 |
| D | 95 | 95 | 1.0 | 3.2 |
| E | 52 | 48 | 0.94 | 2.4 |
| F | 31 | 23 | 0.75 | 3.5 |
| G | 97 | 96 | 0.99 | 3.5 |
| H | 96 | 95 | 1.0 | 2.4 |
| I | 97 | 95 | 0.99 | 3.5 |
| J | 96 | 95 | 0.99 | 2.9 |
| K | 94 | 94 | 1.00 | 1.8 |
| L | 96 | 95 | 0.99 | 3.5 |
| M | 89 | 87 | 0.98 | 2.1 |
| Control A | 94 | 90 | 0.97 | 12 |
| Control B | 96 | 93 | 0.97 | 42 |

EXAMPLE 18

Immunoassay for Thyroxine Using Dry Analytical Element

This example illustrates the preparation of a dry analytical element of this invention and its use in a competitive immunoassay to determine the hormone thyroxine in a liquid sample. Two reagents of this invention are compared to a Control reagent in the assays.

Two reagents prepared according to the description in Example 2 were used in this assay. A Control reagent was prepared using the procedures described in EP-A-0 280 556 (noted above). The activating agent used was 1-(1-pyrrolidinylcarbonyl)pyridinium chloride. The reagents were incorporated into standard barium sulfate spreading layers of the elements at two levels: either 25 mg polymer/m$^2$ of layer surface, or 50 mg polymer/m$^2$ of layer surface.

The copolymers used to prepare the reagents were:

Test A: Poly(styrene-co-mono-m & p-vinylbenzyl glutarate) (97.84:2.16 molar ratio), Test B: Poly(styrene-co-mono-2-methacryloylo xyethyl glutarate) (97.84:2.16 molar ratio), and Control: A core/shell polymer particle having a core of poly(styrene-co-ethylene dimethacrylate) (99:1 molar ratio) and a shell of poly[styrene-co-m & p-(2-chloroethylsulfonylmethyl)styrene-co-ethylene dimethacrylate] (94.5:4.5:1 molar ratio).

The structure of the element used in the assay was as follows:

| | | Coverage (g/m$^2$) |
|---|---|---|
| Spreading Layer | Barium sulfate | 108.6 |
| | Reagent with thyroxine antibodies | 0.025 or 0.05 |
| | Cellulose acetate | 8.6 |
| | Estane TM polyurethane (B. F. Goodrich) | 1.08 |
| | Triton TM X-405 surfactant (Rohm and Haas) | 2.1 |
| Subbing Layer 2 | Poly(N-isopropyl-acrylamide) | 13.1 |
| Subbing Layer 1 | Gelatin | 1 |
| | Triethanolamine (pH 7.5) | 0.15 |

|  |  | Coverage (g/m²) |
|---|---|---|
| | Bovine serum albumin | 0.05 |
| | Triton TM X-100 surfactant (Rohm & Haas) | 0.01 |
| | Magnesium chloride | 0.02 |
| | Zinc chloride | 0.001 |
| Gelatin Layer | Hardened gelatin | 10 |
| | Triethanolamine (pH 7.5) | 0.75 |
| | Triton TM X-100 surfactant (Rohm & Haas) | 0.02 |
| | Poly(ethylene terephthalate) Support | |

A series of thyroxine standard solutions varying in concentration from $10^{-5}$ to $10^{-10}$ molar were prepared in the buffer described below from a $1 \times 10^{-3}$ molar thyroxine stock solution in dimethyl sulfoxide. The buffer consisted of phosphate buffered saline (pH 7.4), bovine serum albumin (1%) and 8-anilino-1-naphthalenesulfonic acid ($8.7 \times 10^{-4}$ molar). A solution of alkaline phosphatase-labeled thyroxine was prepared at a concentration of $2.0 \times 10^{-8}$ molar. The labeled analogs were prepared by the method described by Ito et al, Clin.Chem., 30(10), pp. 1682–1685 (1984). The thyroxine standards and the labeled analog solution were mixed 1:1, so that the final concentration of labeled analog was $1.0 \times 10^{-8}$ molar.

Aliquots (10 μl) of this mixture were spotted onto the spreading layer of the element. After 5 minutes incubation at 37° C., a wash solution (10 μl) containing p-nitrophenyl phosphate (15 mmolar) was added to the element to remove uncomplexed labeled analog from any complex formed in the spreading layer. After a one minute incubation, the change in reflection density ($\Delta D_R$) was measured for 30 seconds in the center of the element at 37° C. and 400 nm using a standard spectrophotometer.

The results of the assays for the two thyroxine concentrations are provided in Table XII below. These results show that the thyroxine antibody immobilized on two reagents of this invention in the element provides improved results over the Control reagent. More specifically, the reagents of this invention exhibit a "higher reaction" rate where the thyroxine level is low. Thus, the reagents exhibit high binding reactivity towards the labeled analog and provide a greater working range for the assay. Working range is defined here as the difference in rates at $10^{-10}$ and $10^{-5}$ molar thyroxine.

TABLE XII

| Test | Antibody Coverage (g/m²) | Rate ($\Delta D_R$/min.) $10^{-10}$ molar | $10^{-5}$ molar | Working Range |
|---|---|---|---|---|
| A | 0.05 | 0.072 | 0.005 | 0.067 |
| B | 0.05 | 0.090 | 0.005 | 0.085 |
| Control | 0.05 | 0.042 | 0.001 | 0.041 |
| A | 0.10 | 0.103 | 0.010 | 0.093 |
| B | 0.10 | 0.112 | 0.010 | 0.102 |
| Control | 0.10 | 0.068 | 0.002 | 0.066 |

EXAMPLE 19

Assay for Thyroxine in Dry Element

This example illustrates the practice of this invention to detect thyroxine in a dry analytical element using a competitive binding assay and a horseradish peroxidase-labeled conjugate.

Two thyroxine antibodies were used: (a) obtained from BiosPacific (clone 035-A2206A), and (b) obtained from Beckman Instruments (#684823). They were covalently attached to particles of poly-[styrene-co-3-(p-vinylbenzylthio)propionic acid] (97.59:2.41 molar ratio) using the procedure described in Example 2 and 1-(1-pyrrolidinylcarbonyl)pyridinium chloride as an activating agent. The resulting reagents were incorporated into a spreading layer of the analytical element illustrated below.

|  |  | Coverage (g/m²) |
|---|---|---|
| Spreading Layer | Reagent (1.4 μm particles) | 0.15 |
| | Particles of poly[m- & p-vinyltoluene (64:36)-co-methacrylic acid](98:2 weight ratio) (30 μm) | 129 |
| | 3,4-Bis(4-dimethylamino-phenyl)-2-(3,5-dimethoxy-4-hydroxyphenyl)imidazole | 0.2 |
| | 3-(4-morpholino)propanesulfonic acid buffer | 0.2 |
| | Zonyl TM FSN surfactant (DuPont) | 0.054 |
| | Xanthan gum (Kelzan TM from Kelco) | 0.065 |
| | 5,5-Dimethyl-1,3-cyclohexanedione | 0.050 |
| | Poly(methyl acrylate-co-sodium 2-acrylamido-2-methyl-propanesulfonate-co-2-acetoacetxyethyl-methacrylate) (90:4:6 weight ratio) | 2.58 |
| Gelatin Layer | Hardened gelatin | 10 |
| | Potassium phosphate | 0.68 |
| | Triton TM X-100 surfactant (Rohm & Haas) | 0.02 |
| | 4'-hydroxyacetanilide | 0.15 |
| | Poly(ethylene Terephthalate) Support | |

A series of thyroxine standard solutions were prepared in the buffer described below from a $10^{-3}$ molar stock solution (in dimethyl sulfoxide) to have concentration varying from $10^{-5}$ to $10^{-10}$ molar. The buffer consisted of 3-(4-morpholino)propanesulfonic acid buffer (0.2 molar, pH 7), 4-hydroxyacetanilide (0.01 molar), 8-anilinonaphthalene-1-sulfonic acid ($8.7 \times 10^{-4}$ molar) and bovine gamma globulin (0.1%). A horseradish peroxidase-labeled thyroxine analog solution was prepared at a concentration of $2 \times 10^{-9}$ molar. The analog was prepared using the method described by Kunst et al, Clin.Chem., 34(9), pp. 1830–1833 (1988).

The analog and standard solutions were mixed 1:1 so that the final concentration of the analog was $10^{-9}$ molar. A Control solution containing no thyroxine was also tested.

Aliquots (10 μl) of the mixtures were spotted onto the spreading layer of the element. After incubation at 37° C. for 5 minutes, a wash solution containing hydrogen peroxide (10 μl) was added to wash uncomplexed analog from the complex in the center of the element. After incubation for 40 seconds at room temperature, the change in reflection density ($\Delta D_R$) was measured for 30 seconds in the center of the element at 37° C. and 680 nm using a standard spectrophotometer. The Williams-Clapper transform (J.Opt.Soc.Am., 43, 595, 1953) was used to convert the reflection densities to transmittance values ($\Delta D_T$). The results are shown in Table XIII below. They show substantial changes in the rate in the desired thyroxine concentration range using the two reagents of this invention.

TABLE XIII

| Thyroxine Concentration (Molar) | Rate ($\Delta D_T$/Min.) | |
| --- | --- | --- |
| | Reagent (a) | Reagent (b) |
| Control | 0.0877 | 0.0914 |
| $10^{-10}$ | 0.0899 | 0.0942 |
| $10^{-9}$ | 0.0888 | 0.0941 |
| $10^{-8}$ | 0.0802 | 0.0867 |
| $10^{-7}$ | 0.0398 | 0.0396 |
| $10^{-6}$ | 0.0226 | 0.0245 |
| $10^{-5}$ | 0.0147 | — |

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A method for the determination of a specific binding ligand comprising:
  A. forming a water-insoluble specific binding complex of a specific binding ligand of interest, or a receptor therefor, with a reagent comprising:
    (I) a water-insoluble particle composed of a copolymer having recurring units derived from:
      (a) from about 60 to about 99.8 mole percent of one or more ethylenically unsaturated polymerizable oleophilic monomers which provide hydrophobicity to said copolymer,
      (b) from about 0.2 to about 40 mole percent of one or more ethylenically unsaturated polymerizable monomers having a reactive carboxy group, or salt thereof, and represented by the structure:

$$CH_2=C-L-C-OM$$

with R above the C and C (=O) above the second C wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain,
said organic linking group further defined as having two or more divalent groups selected from the group consisting of alkylene, arylene, alkylenearylene and arylenealkylene which are connected to each other or terminated with an oxy, thio, imino, carbonyloxy, carbonylimino, ureylene or sulfonylimino group, and
      (c) from 0 to about 15 mole percent of one or more additional ethylenically unsaturated polymerizable monomers other than those identified in categories (a) and (b) above, and
    (II) a biologically active substance covalently attached to said particle through said reactive carboxy group or salt thereof, said substance being specifically reactive with either said ligand or a receptor therefor, and
  B. detecting the presence of said complex as an indication of the presence or amount of said ligand in said specimen.

2. The method of claim 1 wherein said ligand is a protein, carbohydrate, hapten, hormone or drug, and said receptor is an antibody for said protein, carbohydrate, hapten, hormone or drug.

3. The method of claim 1 wherein said ligand is biotin or a derivative thereof, and said receptor is avidin or a derivative thereof.

4. The method of claim 1 wherein said ligand is a single-stranded nucleic acid, and said receptor is a second single-stranded oligonucleotide which is substantially complementary to said nucleic acid.

5. A competitive binding assay for the determination of a specific binding ligand comprising:
  A. contacting a specimen suspected of containing a water-soluble specific binding ligand with a water-soluble receptor therefor, and with a reagent comprising:
    (I) a water-insoluble particle composed of a copolymer having recurring units derived from:
      (a) from about 60 to about 99.8 mole percent of one or more ethylenically unsaturated polymerizable oleophilic monomers which provide hydrophobicity to said copolymer,
      (b) from about 0.2 to about 40 mole percent of one or more ethylenically unsaturated polymerizable monomers having a reactive carboxy group, or salt thereof, and represented by the structure:

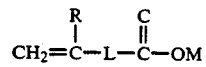

$$CH_2=C-L-C-OM$$

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain,
said organic linking group further defined as having two or more divalent groups selected from the group consisting of alkylene, arylene, alkylenearylene and arylenealkylene which are connected to each other or terminated with an oxy, thio, imino, carbonyloxy, carbonylimino, ureylene or sulfonylimino group, and
      (c) from 0 to about 15 mole percent of one or more additional ethylenically unsaturated polymerizable monomers other than those identified in categories (a) and (b) above, and
    (II) molecules of said ligand covalently attached to said particle through said reactive carboxy group or salt thereof,
to form specific binding complex (i) between said receptor and said ligand, and specific binding complex (ii) between said receptor and said water-insoluble reagent, and
  B. after separating said complexes (i) and (ii), detecting the presence of either complex as an indication of the presence or amount of said ligand in said specimen.

6. A method for the determination of an immunological species comprising:
  A. contacting a specimen suspected of containing an immunological species with a reagent comprising:
    (I) a water-insoluble particle composed of a copolymer having recurring units derived from:

(a) from about 60 to about 99.8 mole percent of one or more ethylenically unsaturated polymerizable oleophilic monomers which provide hydrophobicity to said copolymer, (b) from about 0.2 to about 40 mole percent of one or more ethylenically unsaturated polymerizable monomers having a reactive carboxy group, or salt thereof, and represented by the structure:

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, said organic linking group further defined as having two or more divalent groups selected from the group consisting of alkylene, arylene, alkylenearylene and arylenealkylene which are connected to each other or terminated with an oxy, thio, imino, carbonyloxy, carbonylimino, ureylene or sulfonylimino group, and (c) from 0 to about 15 mole percent of one or more additional ethylenically unsaturated polymerizable monomers other than those identified in categories (a) and (b) above, and (II) a receptor for said species covalently attached to said particle through said reactive carboxy group or salt thereof, to form a water-insoluble immunological complex of said species with said receptor, and B. after separating uncomplexed materials from said complex, detecting the presence of said complex as an indicator of the presence or amount of said immunological species in said specimen.

7. The method of claim 6 wherein said immunological species is an antigenic material and said receptor is an antibody for said antigenic material.

8. The method of claim 6 wherein said immunological species is an antibody and said receptor is an antigenic material specific for said antibody.

9. The method of claim 6 wherein said immunological species is a first antibody and said receptor is a second antibody directed to said first antibody.

10. The method of claim 6 wherein said uncomplexed materials are separated from said immunological complex by filtration with a microporous membrane.

11. The method of claim 6 wherein said reagent is immobilized on a microporous filtration membrane.

12. The method of claim 6 wherein, either prior to, simultaneously with or subsequently to the formation of said water-insoluble immunological complex, said immunological species is reacted with a water-soluble specific binding component specifically reactive therefor.

13. The method of claim 12 wherein said specific binding component is labeled for detection.

14. The method of claim 13 wherein said label is an enzyme or radioisotope.

15. The method of claim 6 wherein said immunological species is human chorionic gonadotropin, Streptococcus A or a microorganism associated with periodontal disease.

16. An assay for the determination of a specific binding ligand comprising:

detecting the presence or amount of a water-insoluble specific binding complex formed between a specific binding ligand of interest and a receptor for said ligand as an indication of the determination of said specific binding ligand of interest, the receptor provided as a component of a reagent comprising:

(I) a water-insoluble particle composed of a copolymer having recurring units derived from:

(a) from about 60 to about 99.8 mole percent of one or more ethylenically unsaturated polymerizable oleophilic monomers which provide hydrophobicity to said copolymer, (b) from about 0.2 to about 40 mole percent of one or more ethylenically unsaturated polymerizable monomers having a reactive carboxy group, or salt thereof, and represented by the structure:

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, said organic linking group further defined as having two or more divalent groups selected from the group consisting of alkylene, arylene, alkylenearylene and arylenealkylene which are connected to each other or terminated with an oxy, thio, imino, carbonyloxy, carbonylimino, ureylene or sulfonylimino group, and (c) from 0 to about 15 mole percent of one or more additional ethylenically unsaturated polymerizable monomers other than those identified in categories (a) and (b) above, and (II) the receptor for said ligand being covalently attached to said particle through said reactive carboxy group or salt thereof.

17. An analytical separation method comprising:

A. passing a specimen containing a mixture of biologically active substances over an affinity chromatography reagent comprising:

(I) a water-insoluble particle composed of a copolymer having recurring units derived from:

(a) from about 60 to about 99.8 mole percent of one or more ethylenically unsaturated polymerizable oleophilic monomers which provide hydrophobicity to said copolymer, (b) from about 0.2 to about 40 mole percent of one or more ethylenically unsaturated polymerizable monomers having a reactive carboxy group, or salt thereof, and represented by the structure:

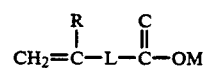

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain, said organic linking group further defined as having two or more divalent groups selected from the group consisting of alkylene, arylene, alkylenearylene and arylenealkylene which are connected to each other or terminated with an oxy, thio, imino, carbonyloxy, carbonylimino, ureylene or sulfonylimino group, and (c) from 0 to about 15 mole percent of one or more additional ethylenically unsaturated polymerizable monomers other than those identified in categories (a) and (b) above, and (II) a specific binding substance covalently attached to said particle through said reactive carboxy group, said specific binding substance being specific to one or more predetermined biologically active substances in said specimen mixture of biologically active substances to form a complex of said reagent with said predetermined substances, and B. collecting either the one or more complexed predetermined substances or one or more substances remaining in the eluent.

* * * * *